(12) United States Patent
Jung

(10) Patent No.: US 6,469,193 B1
(45) Date of Patent: Oct. 22, 2002

(54) EFFICIENT SYNTHESIS OF ALKYL CARBONATES

(75) Inventor: Kyung Woon Jung, Tampa, FL (US)

(73) Assignee: University of South Florida, Tampa, FL (US)

(*) Notice: Subject to any disclaimer, the term of this patent is extended or adjusted under 35 U.S.C. 154(b) by 0 days.

(21) Appl. No.: 09/513,218

(22) Filed: Feb. 25, 2000

Related U.S. Application Data

(60) Provisional application No. 60/149,905, filed on Aug. 23, 1999, provisional application No. 60/138,656, filed on Jun. 14, 1999, provisional application No. 60/126,151, filed on Mar. 25, 1999, and provisional application No. 60/121,867, filed on Feb. 26, 1999.

(51) Int. Cl.$^7$ .......................... C07C 68/00; C07C 69/96
(52) U.S. Cl. ...................................... 558/275; 558/260
(58) Field of Search ................................... 558/275, 260

(56) References Cited

PUBLICATIONS

Chu, F. et al. : Cs2CO3 promoted O–Alkylation of alcohols for the preparation of mixed alkyl carbonates. Tetrahed. lett. vol. 40, pp. 1847–1850, 3.5.1999.*

Fang, S. et al.: Direct synthesis of dimethyl carbonate from carbon dioxide and methanol catalyzed by base. Applied Catalysis, vol. 142, pp. L1–L3, 1996.*

* cited by examiner

*Primary Examiner*—Charanjit S. Aulakh
(74) *Attorney, Agent, or Firm*—Saliwanchik, Lloyd & Saliwanchik

(57) ABSTRACT

Efficient synthetic methods towards mixed aliphatic carbonates through the three component couplings of aliphatic alcohols, alkyl halides and carbon dioxide in the presence of cesium carbonate and tetrabutylammonium iode (TBAI). Due to their enhanced nucleophilicities, cesium alkoxides are smoothly incorporated into $CO_2$, allowing for mild reaction conditions such as ambient temperatures and short reaction durations. Various primary and secondary substrates are compatible under the standard conditions, offering high yields, while chiral templates such as α-hydroxy carbonyls are resistant to racemization.

18 Claims, 8 Drawing Sheets

General Synthetic Methodology

Carbonate Formation Using Various Substrates

| Entry | Alcohol (ROH) | Halide (R'X) | Time | Yield |
|---|---|---|---|---|
| 1 | Ph(CH₂)₃CH₂OH | n-BuBr | 3.5 h | 94% |
| 2 | Ph(CH₂)₃CH₂OH | Br–CH₂–CO₂tBu | 5 h | 95% |
| 3 | Ph(CH₂)₃CH₂OH | sec-BuBr | 23 h | 98% |
| 4 | PhCH₂CH(OH)CH₃ | Br–CH₂–CO₂tBu | 5 h | 96% |
| 5 | menthol | n-BuBr | 5 h | 96% |
| 6 | PhCH₂CH(OH)CH₃ | n-BuBr | 4.5 h | 92% |
| 7 | Ph(CH₂)₃CH₂OH | BnCl | 2.5 h | 94% |
| 8 | PhCH₂CH(OH)CH₃ | BnCl | 3 h | 98% |
| 9 | Ph(CH₂)₃CH₂OH | Allyl Bromide | 4 h | 91% |

FIG. 2

Carbonate Formation Using Chiral Templates

| Entry | Alcohol (ROH) | Halide (R'X) | Time | Yield |
|---|---|---|---|---|
| 1 | Ph-CH(OH)-C(=O)-OMe | BnBr | 3 h | 65% |
| 2 | Ph-CH(OH)-C(=O)-OMe | MPMCl | 3 h | 92% |
| 3 | 3-hydroxy-4,4-dimethyl-γ-butyrolactone | BnCl | 3 h | 90% |
| 4 | 3-hydroxy-4,4-dimethyl-γ-butyrolactone | MPMCl | 3 h | 94% |
| 5 | Me-CH(OH)-C(=O)-OEt | BnCl | 3 h | 90% |
| 6 | Me-CH(OH)-C(=O)-OEt | MPMCl | 3 h | 94% |
| 7 | MeO-C(=O)-CH(OH)-CH2-C(=O)-OMe | BnCl | 3 h | 65% |
| 8 | Ph-CH2-CH(OH)-C(=O)-OBn | BnCl | 3 h | 85% |

FIG. 3

Solid Phase Synthesis of Carbonates

| Entry | Alcohol (ROH) | Yield |
|---|---|---|
| 1 | CH$_3$(CH$_2$)$_7$OH | 54% |
| 2 | CH$_3$(CH$_2$)$_9$OH | 55% |
| 3 | PhCH$_2$OH | 63% |
| 4 | Ph(CH$_2$)$_3$OH | 65% |
| 5 | 4-O$_2$N-C$_6$H$_4$-CH$_2$OH | 35% |

Improved Solid Phase Synthesis of Carbonates

| Entry | Alcohol (ROH) | Yield |
|---|---|---|
| 1 | CH₃(CH₂)₇CH₂OH (n-nonanol) | 54% |
| 2 | CH₃(CH₂)₉CH₂OH (n-undecanol) | 77% |
| 3 | PhCH₂OH (benzyl alcohol) | 97% |
| 4 | Ph(CH₂)₃OH | 65% |
| 5 | 4-O₂N-C₆H₄-CH₂OH | 77% |
| 6 | cyclohexanol | 98% |
| 7 | 3,3-dimethyl-2-butanol | 98% |
| 8 | Menthol | 83% |
| 9 | Ph-CH(OH)-CO₂Me | 76% |
| 10 | Ph-CH₂-CH(OH)-CO₂Bn | 63% |
| 11 | (S)-3-hydroxy-γ-butyrolactone | 58% |

Improved Solid Phase Synthesis of Carbonates

| Entry | Halide (RX) | Yield |
|---|---|---|
| 1 | CH3(CH2)7CH2Br | 97% |
| 2 | CH3(CH2)9CH2Br | 99% |
| 3 | PhCH2Br | 91% |
| 4 | 4-O2N-C6H4-CH2Br | 83% |
| 5 | 4-MeO-C6H4-CH2Br | 83% |
| 6 | (CH3)2CHBr | 28% |

Intramolecular Carbonylation

US 6,469,193 B1

EFFICIENT SYNTHESIS OF ALKYL CARBONATES

RELATED APPLICATIONS

The present application claims priority to U.S. Provisional application No. 60/121,867, filed Feb. 26, 1999, U.S. Provisional application No. 60/126,151, filed Mar. 25, 1999, U.S. Provisional application No. 60/138,656, filed Jun. 14, 1999, and U.S. Provisional application No. 60/149,905, filed Aug. 23, 1999 each of which is incorporated herein by reference in its respective entirety.

FIELD OF THE INVENTION

The present invention relates to an efficient carbonate synthesis by way of cesium carbonate promoted alkylation of various alcohols with organic electrophiles in the presence of carbon dioxide. In particular, the invention relates to the alkylation of aliphatic alcohols with alkyl halides.

BACKGROUND OF THE INVENTION

Organic carbonates exhibit unique physical and chemical properties, accommodating a variety of applications. For example, carbonate functionalities have been used as protecting groups or intermediates in numerous syntheses. They have also been utilized as synthetic intermediates in functional transformations and functional group manipulations such as ester formation, glycosylation, urethane synthesis, linker preparation on solid phase synthesis, and so on. Alkylation with alkyl carbonates is also a prominent application in synthesis.

Organic carbonates have been used as fuel additives, (gasoline, diesel and so on), dyes, and lubricating oils, (for example, in refrigerators). Mixed carbonate ester derivatives of quinophthalone dyes have been prepared and utilized for thermal imaging. Carbonate has been used as a bridging member between anthraquinone dyestuffs and synthetic organic fibers, especially polyethylene glycol terephthalate fibers.

Some carbonates have been used as polymerization catalysts. For example, diethyl carbonate catalyzed propylene polymerization while isocynates were polymerized with polyols in the presence of a catalytic amount of an organic carbonate salt. More importantly, numerous organic carbonates are used as monomers for various polymerization. Typical examples encompass cyclic carbonates such as trimethylene carbonate as well as acyclic carbonates including diethylene glycol bis(allyl carbonate), (DADC).

Carbonates are also very important in the polymer industry. For example, DADC is widely used as a polymerization monomer for the production of an optical plastic in the manufacturing of lenses, safety glasses, guards, watch glasses, and instrument windows.

Aliphatic carbonates or carbonate functionalities have shown pharmacologic activities including protein kinase inhibition, antibacterial activity, and stimulatory effect on the central nerve system.

Carbonates often play an important role in pharmacology as demonstrated by 6'-carbonate esters of zearalanol promoting growth in ruminants and also reducing the severity of vasomotor symptoms associated with menopause in women.

Biodegradable organic carbonates have been implemented in medicinal fields as prodrugs, drug delivery materials, sutures, surgical implant materials, and so on. Some carbonate polymers, resistant to biodegradation, are strongly believed to provide good materials for artificial skin and bone structure.

Thus, in view of the vast and increasingly important role played by carbonates, a protocol for efficient carbonate synthesis is desirable.

Common methods leading to carbonates are categorized into alcoholysis of phosgene or its derivatives, organic carbonate exchange, carbon dioxide alkylation, and inorganic carbonate alkylation. These methods employ the usage of strongly basic conditions, special carriers, or catalysts, and elevated temperatures or pressures. In addition, the bases used, such as potassium carbonate and organic amines, require high temperatures (i.e., 80° C.) and/or lengthy reaction times (i.e., 20 hours).

Thus, known methods for the syntheses of alkyl carbonates have shortcomings including the following:

1. Use of toxic or expensive reagents such as phosgene and silver salts. 2. Employment of harsh reaction conditions such as high temperature and pressure. 3. Low yields due to the inconvenient and inefficient processes. 4. Difficulties in purification because of the complicated product mixture.

5. Limitations in compatible and available substrates.

Above all, the existing methods such as alcoholysis of phosgene or its derivatives, organic carbonate exchange, carbon dioxide alkylation and inorganic carbonate alkylation lack in generality for the carbonate synthesis, especially unsymmetrical aliphatic carbonates. Although carbonate exchange methodologies provide mixed alkyl carbonates, the desired products are part of the statistical mixtures, making these syntheses inapplicable to practical utilities.

A need therefore exists for an improved process for the synthesis of carbonates which avoids the aforementioned disadvantages and drawbacks.

BRIEF SUMMARY OF THE INVENTION

It is therefore an object of the present invention to provide an improved process for the synthesis of carbonates which avoids the aforementioned disadvantages and drawbacks.

It is a further object of the present invention to provide a process that obviates the use of toxic or expensive reagents.

It is a further object of the present invention to provide a process that obviates harsh reaction conditions.

It is a further object of the present invention to provide improved and purer carbonate yields.

It is a further object of the present invention to provide a methodology for synthesizing new biomolecules.

It is a further object of the present invention to provide new polymerization materials.

It is a further object of the present invention to provide carbonate synthesis methods that are facile on solid phase, contributing to the generation of a wide variety of alkyl carbonate libraries.

Reported herein is the efficient synthetic protocol for mixed alkyl carbonates, which are generated by cesium carbonate promoted O-alkylation of various aliphatic alcohols with alkyl halides in the presence of carbon dioxide. Unlike the known methods, these methodologies utilize two different coupling partners and prepare the unsymmetrical alkyl carbonates selectively. Use of cesium base is preferred for the intended transformation and the reaction conditions are mild, e.g., room temperature and atmospheric pressure. Employment of tetrabutylammonium iodide is also preferred in certain cases to yield efficient and rapid synthesis. This technology is successfully applied to the synthesis of symmetric carbonates. As in the solution phase, all these methods are facile on solid phase, contributing to the generation of a wide variety of alkyl carbonate libraries.

BRIEF DESCRIPTION OF THE DRAWINGS

FIG. 2 illustrates the reaction of alcohols under the conditions of FIG. 1, with various alkyl halides.

FIG. 3 illustrates carbonate formation using chiral templates.

DETAILED DESCRIPTION OF THE INVENTION

Figure 1:
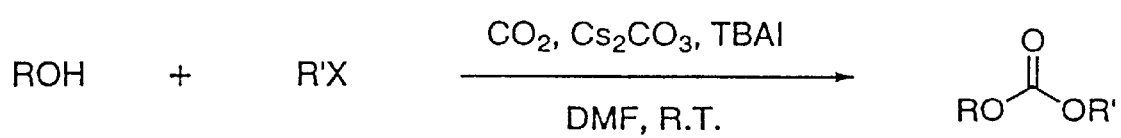
FIG. 1 illustrates ligating alcohols to alkyl halides to form alkyl carbonates.

FIG. 1 illustrates ligating alcohols to organic electrophiles through a $CO_2$ bridge derived from $CO_2$, in the presence of tetrabutylammonium iodide (TBAI), resulting in the exclusive formation of carbonates in excellent yields. These methodologies are carried out successfully on both solution phase and solid phase. Preferably, the alcohols are aliphatic alcohols (ROH), the organic electrophiles are alkyl halides (R'X), and alkyl carbonates are formed.

FIG. 2 illustrates the reaction of both primary and secondary alcohols under the aforementioned standard conditions, with various alkyl halides. Each reaction yields the desired alkyl carbonates in high yields. These transformations are completed quickly at room temperature, affording much milder conditions than prior methods. In addition, through this technique, one is able to prepare certain carbonates which are otherwise difficult to generate.

As shown, outstanding yields and selectivities are obtained, even though some of these substrates have shown difficulties for carbonate linkage installation, due to steric hindrance, hydrolysis tendency and vulnerability towards strong bases in the previously reported methods.

Both primary alcohols and secondary alcohols react smoothly with primary halides, producing excellent yields. Compared to primary alcohols, carbonate formation from secondary alcohols need a longer time due to the steric hindrance and less acidity of the alcohol protons. Amazingly, under the conditions set forth herein, a secondary bromide can convert an unreactive primary alcohol to a desired carbonate exclusively. This conversion is very difficult to obtain using other methodologies. In addition, the disclosed protocol is efficient for benzyl and allyl carbonate protection, which are well-resorted in peptide synthesis for their general stability and convenient deprotection. Averting the employment of benzyl chloroformate and organic bases, this method exhibits handling convenience, easy purification, and high conversion and selectivity. FIG. 3 illustrates subjecting chiral templates prone to stereochemical loss to the aforementioned standard conditions, giving rise to the formation of the desired alkyl carbonates in satisfactory yields. In most cases, racemization is not observed within the detection limits. This technology facilitates the synthesis of various chiral compounds which have not been available due to the lack of general methods.

Figure 4:
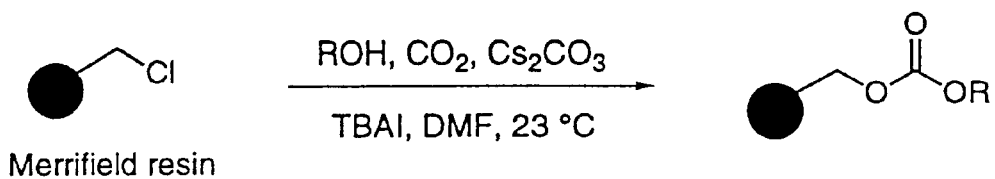
FIGS. 4 and 5 illustrate carbonate synthesis on solid phase using Merrifield resin.
Figure 5:
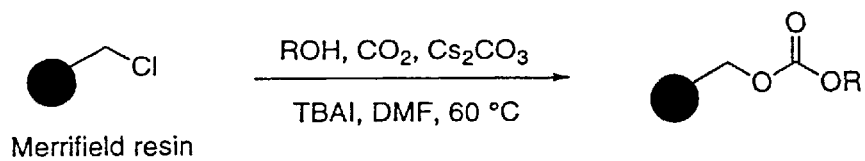

FIGS. 4 and 5 illustrate the successful implementation of carbonate synthesis on solid phase using Merrifield resin. This method allows new functionalities and new linkers on solid phase synthesis, enhancing the efficiency of combinatorial synthesis.

Figure 6:
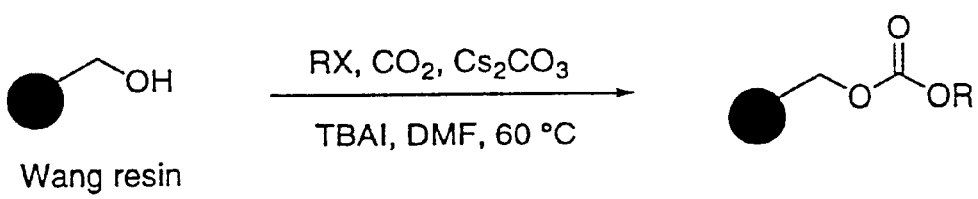
FIG. 6 illustrates carbonate synthesis on solid phase using Wang resin.

FIG. 6 illustrates the successful implementation of carbonate synthesis on solid phase using Wang resin.

Figure 7:
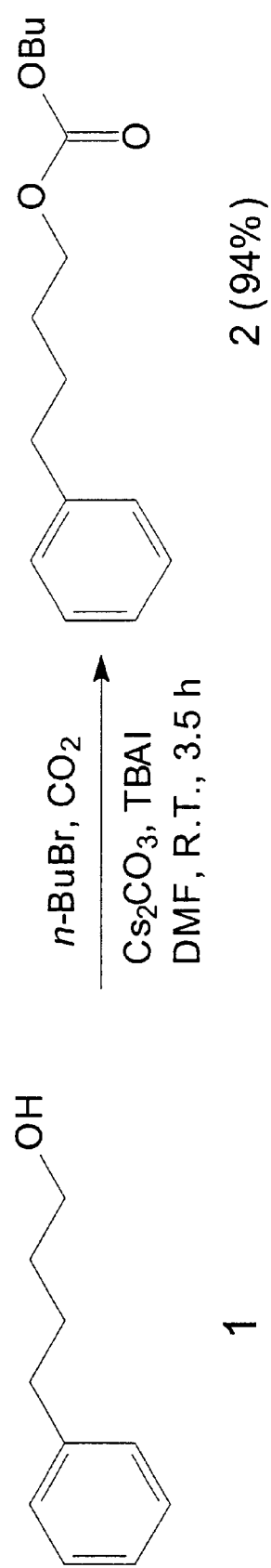
FIG. 7 illustrates a preferred embodiment of carbonate formation.

FIG. 7 illustrates a preferred embodiment wherein the employment of N,N-dimethylformamide (DMF), tetrabutylammonium iodide (TBAI) gives the ideal result for carbonate 2 formation.

Figure 8:
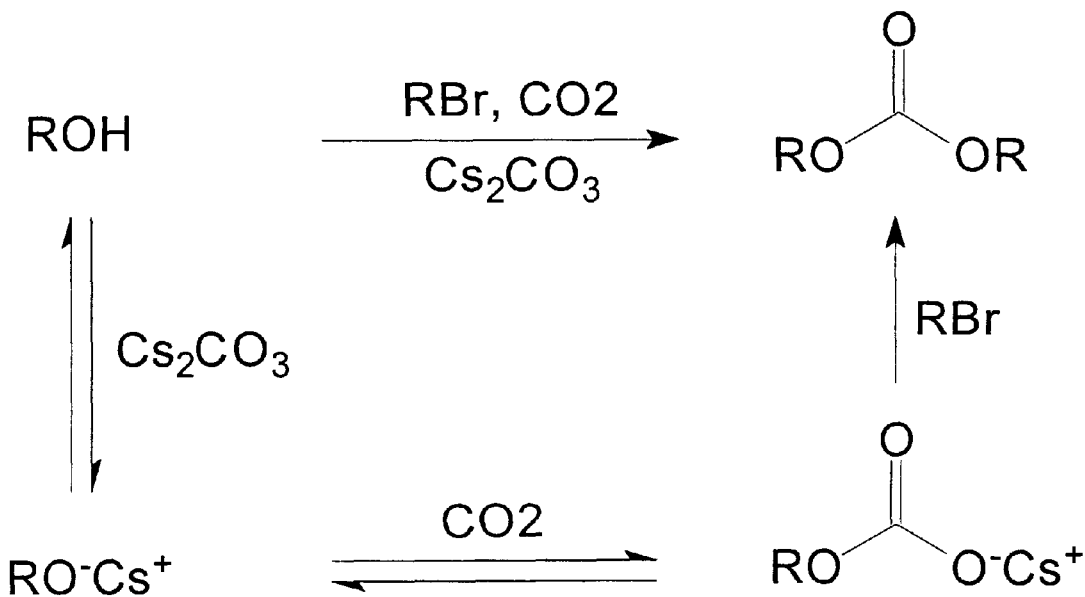
FIG. 8 illustrates a mono-alkylated carbonate intermediate A.

FIG. 8 illustrates a mono-alkylated carbonate intermediate, which is the product of the reaction between the alkoxide of the alcohol and carbon dioxide. The observed cesium effect is attributed to the increased ionic and nucleophilic characters of the alkoxide and mono-alkylated carbonate anion. High solubility of cesium carbonate in DMF also assists in maintaining a higher concentration of alkoxide.

Figure 9:
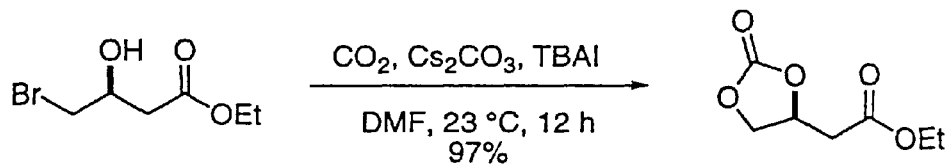
FIG. 9 illustrates intramolecular carbonylation.

FIG. 9 illustrates intramolecular carbonylation. Examples of intramolecular carbonylation are disclosed infra, for example as set forth in Example 22.

In summary, a pragmatic methodology under amazingly mild conditions is disclosed for carbonate formation from alcohols. Outstanding results are obtained for a large variety of substrates in carbonate preparation from both primary alcohols and secondary alcohols, as well as benzyl carbonate and allyl carbonate protection. Through this methodology, newly designed biomolecules can be synthesized.

Using the methods of the invention, the reactions are rapid (2–5 hours) at room temperature, giving high yields (usually greater than 90%). Compared to procedures known in the art, the present invention enhances the yields of the desired carbonates. Moreover, the synthesis of many carbonates is not feasible under conditions known in the art, while the process of the current invention facilitates the synthesis of various symmetrical and mixed carbonates. For instance, disclosed are the use of sterically hindered alcohols such as menthol and pantolactone as well as chiral substrates without any sterochemical loss. In addition, the methods of the invention allow clean transformations, resulting in no side products or impurities in most cases, which alleviates the need for any isolation or purification steps.

Thus, an efficient protocol for the synthesis of alkyl carbonates utilizing cesium bases and carbon dioxide is described. In this O-alkylation, primary and secondary alcohols are reacted with various alkyl halides. This methodology offers a general synthetic method of mixed and symmetric carbonates for a variety of applications.

The synthesis disclosed herein requires one step while prior routinely used methods need 1–3 steps. Some methods use toxic and corrosive reagents such as phosgene, while the present methods are much safer and more reliable than any known protocols. Because of excellent substrate versatility, it is possible to make a plethora of new alkyl carbonates useful in research and industry.

EXPERIMENTAL SECTION

General Procedures

Proton nuclear magnetic resonance ($^1$H NMR) spectra are recorded in deuterated $CDCl_3$ on a Bruker AMX-360 (360 MHz). Chemical shifts are reported in parts per million (ppm, d) relative to either tetramethylsilane (d 0.00 ppm) or trace amounts of the undeuterated chloroform residue (CDCl$_3$, d 7.27 ppm) as an internal standard. $^1$H NMR splitting patterns are designated as singlet (s), doublet (d), triplet (t), quartet (q) and multiplet (m). Coupling constants are presented in hertz (Hz). Carbon nuclear magnetic resonance ($^{13}$C NMR) spectra are recorded on a Bruker AMX-360 (90 MHNz). Chemical shifts are reported in ppm (d) relative to the central line of the CDCl$_3$ triplet (d 77.0 ppm). Infrared spectra (IR) are recorded on a Nicolet FT-IR spectrometer 550. Absorption maxima are reported in wavenumbers (cm$^{-1}$). Elemental analysis is performed by Atlantic Microlab, Inc.

Analytical thin layer chromatography (TLC) is carried out on EM TLC plates precoated with silica gel 60F$_{254}$ (250 mm layer thickness). Compounds are visualized on the TLC plate by either a UV light or p-anisaldehyde charring solution (18 mL p-anisaldehyde, 7.5 mL glacial acetic acid, 2.5 mL concentrated sulfuric acid in 675 mL absolute ethanol). Fisher chromatographic silica gel (170–400 mesh) is utilized for flash column chromatography (FCC). Eluent systems for FCC, as well as TLC, are reported in v/v ratios.

When water-sensitive reactions are involved, glassware is flame-dried or oven-dried and purged with nitrogen. Tetrahydrofuran (THF) and diethyl ether (Et$_2$O) are purified from sodium and benzophenone. Acetonitrile and methylene chloride are distilled from calcium hydride. All other commercially available reagents and solvents are used without further purification unless otherwise indicated.

Enantiomeric excess of all carbonate compounds is calculated by $^1$H NMR after deprotection of carbonate using hydrogenolysis, and then preparation of chiral derivative.

EXAMPLE 1
Preparation of Carbonate A1 at Room Temperature

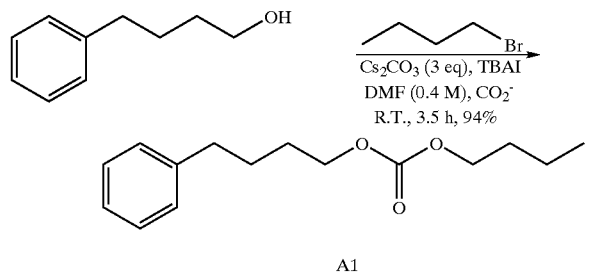

To a solution of 4-phenyl-1-butanol (100 mg, 0.67 mmol) in anhydrous N,N-dimethylformamide (1.6 mL, 0.4 M), cesium carbonate (625 mg, 2.10 mmol, 3 eq) and tetrabutylammonium iodide (208 mg, 0.67 mmol, 1 eq) are added. Carbon dioxide gas (flow rate>>25–30 mL/min) is bubbled through the solution for a couple of minutes before 1-bromobutane (274 mg, 0.22 mL, 2.0 mmol) is added into the solution. The reaction proceeds at room temperature with CO$_2$ gas bubbling for 3.5 hours after which all the starting material (4-phenyl-1-butanol) is consumed. The reaction mixture is then poured into DI water (30 mL) and extracted by 3:1 hexanes-EtOAc (60 mL) thoroughly. The organic layer is washed by DI water (2' 30 mL), brine (30 mL) and dried over sodium sulfate. The solvent is evaporated and the remaining residue is subjected to flash column chromatography (9:1 hexanes-EtOAc) affords A1 (157 yielding, 94%) as clear a liquid.

Data for A1: R$_f$0.49 (9:1 hexanes-EtOAc); IR (thin film) 3082, 3061, 3028, 2958, 2896, 1742, 1602, 1498, 1457, 1399, 1259, 1057, 1016, 932, 793, 746, 699 cm$^{-1}$; $^1$H NMR (360 MHz, CDCl$_3$) d 0.95–1.00 (t, J=7.4 Hz, 2H), 1.40–1.50 (m, J=7.4 Hz, 2H), 1.64–1.72 (m, 2H), 1.72–1.77 (m, 4H), 2.64–2.70 (m, 2H), 4.13–4.20 (m, 4H), 7.19–7.3 (m, 5H); $^{13}$C NMR (90 MHz, CDCl$_3$) d 13.9, 19.2, 27.8, 28.6, 31.0, 35.7, 68.0, 126.2, 128.6, 128.7, 142.2, 155.7. EM Anal. Calcd. for C$_{15}$H$_{22}$O$_3$: C, 71.97; H, 8.86. Found: C, 72.02; H, 8.78.

EXAMPLE 2

Preparation of Carbonate A2

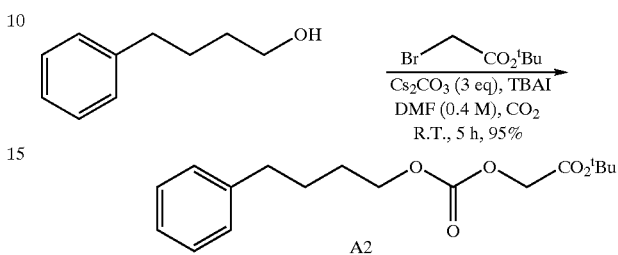

4-Phenyl-1-butanol (100 mg, 0.67 mmol) is dissolved in anhydrous N,N-dimethylformamide (3.2 mL) to make a 0.2 M solution. Tetrabutylammoium iodide (208 mg, 0.67 mmol, 1 eq) and cesium carbonate (625 mg, 2.0 mmol, 3 eq) are added to the solution under vigorous stirring. After carbon dioxide gas is allowed to pass through the reaction suspension for two minutes, tert-butyl bromoacetate (195 mg, 0.19 mL, 1.5 eq) is added to the well stirring reaction mixture. The reaction proceeds at ambient temperature with CO$_2$ bubbling through for a period of about five hours after which 4-phenyl-1-butanol is consumed. The reaction is then extracted by 3:1 hexanes-EtOAc (30 mL), washed by DI water (2' 30 mL) and brine (30 mL) and dried over anhydrous sodium sulfate. Removal of solvent in vacuo and commitment to flash column chromatography (9:1 hexanes-EtOAc) affords desired carbonate A2 (195 mg, 95%) as colorless oil: R$_f$0.43 (9:1 hexanes-EtOAc); IR (neat film) 3065, 3033, 2980, 2940, 2861, 1756, 1607, 1501, 1453, 1290, 1223, 1163, 1035, 793, 753, 699; $^1$H NMR (360 MHz, CDCl$_3$) 1.50 (s, 9H), 1.71–1.76 (m, 4H), 2.63–2.67 (t, J=7.1 Hz, 2H), 4.19–4.23 (t, J=7.2 Hz, 2H), 4.51 (s, 2H), 7.17–7.29 (m, 5H); $^{13}$C NMR (90 MHz, CDCl$_3$) 27.12, 27.67, 27.89, 35.05, 63.32, 68.04, 82.15, 125.55, 128.03, 128.10, 141.55, 154.62, 166.25. EM Anal. Calcd. for C$_{17}$H$_{24}$O$_5$: C, 66.21; H 7.84. Found: C, 66.29; H, 7.80.

EXAMPLE 3

Preparation of Carbonate A17

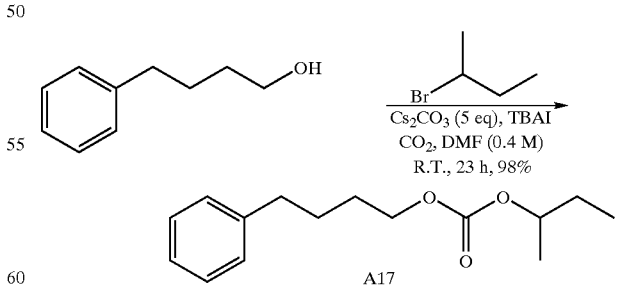

Into a solution of 4-phenyl-1-butanol (150 mg, 1 mmol) in anhydrous N,N-dimethylformamide (2.5 mL, 0.4 M), are added tetrabutylammonium iodide (313 mg, 1 mmol, 1 eq) and cesium carbonate (1.96 g, 5 mmol, 5 eq) under an atmosphere of nitrogen with good stirring. Into the reaction suspension, carbon dioxide is bubbled for a couple of minutes before 2-bromobutane (411 mg, 0.32 mL, 3 mmol, 3 eq) is introduced into the reaction mixture. The reaction is allowed to process at room temperature for twenty-three hours with carbon dioxide gas bubbling through the turbid suspension until all 4-phenyl-1-butanol is completely consumed. The reaction is quenched, poured into deionized water (30 mL) and extracted thoroughly with 3:1 hexanes-EtOAc (60 mL). The resulting organic layer is then washed successively with DI water (2' 30 mL), brine (30 mL) and is dried over anhydrous sodium sulfate. The colorless solution is filtered and evaporated. The residue is purified by flash column chromatography (9:1 hexanes-EtOAc) to yield 164 mg pure, desired carbonate A17 (98%): $R_f$=0.46 (9:1 hexanes-EtOAc); IR (thin film) 3086, 3067, 3029, 2978, 2940, 2884, 1742, 1610, 1502, 1458, 1269, 1099, 796, 752, 704 cm$^{-1}$; $^1$H NMR (360 MHz, CDCl$_3$) 0.94–0.98 (t, J=7.4 Hz, 3H), 1.28–1.31 (d, J=6.2 Hz, 3H), 1.57–1.63 (m, 2H), 1.63–1.74 (m, 4H), 2.66–2.68 (m, 2H), 4.15–4.17 (m, 2H), 4.70–4.76 (m, 1H), 7.19–7.32 (m, 5H); $^{13}$C NMR (90 MHz, CDCl$_3$) 9.67, 19.44, 27.62, 28.35, 28.82, 35.49, 67.56, 76.40, 125.89, 128.38, 128.45, 141.99, 155.08. EM Anal. Calcd C$_{15}$H$_{22}$O$_3$: C, 71.97; H, 8.86. Found: C, 71.85; H, 8.70.

EXAMPLE 4

Preparation of Carbonate A4

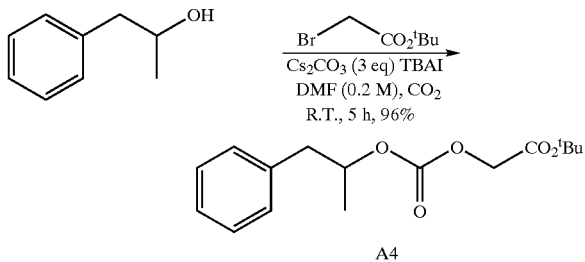

In a solution of 1-phenyl-2-propanol (100 mg, 0.73 mmol) in anhydrous N,N-dimethylformamide (3.7 mL, 0.2 M), is dissolved tetrabutylammonium iodide (230 mg, 0.73 mmol, 1 eq). Cesium carbonate (719 mg, 2.19 mmol, 3 eq) is added and the resulting turbid suspension is well stirred. Then, carbon dioxide gas is passed through the reaction mixture for a couple of minutes before tert-butyl bromoacetate (427 mg, 0.31 mL, 2.19 mmol, 3 eq) is introduced to the reaction system. Carbon dioxide is continuously passed through the reaction mixture at room temperature for five hours until all 1-phenyl-2-propanol is consumed. The reaction mixture is then taken up by 3:1 hexanes-EtOAc (60 mL) and washed successively with DI water (3' 30 mL), saturated brine (30 mL) and dried over anhydrous sodium sulfate. The solvent is removed in vacuo, and the residue is purified by flash column chromatography (9:1 hexanes-EtOAc). The desired product, carbonate A4, is obtained (207 mg, 96%) as a colorless liquid: $R_f$ 0.40 (9:1 hexanes-EtOAc); IR (neat liquid) 3061, 3037, 2987, 2837, 2885, 1750, 1458, 1371, 1290, 1234, 1159, 1060, 786, 755, 699 cm$^{-1}$; $^1$H NMR (360 MHz, CDCl$_3$) 1.29–1.30 (d, J=4.2 Hz, 3H), 1.48 (s, 9H), 2.78–2.82 J$_{AB}$=13.5 Hz, J$_{AX}$=7.0 Hz, 1H), 3.03–3.09 (ABX, J$_{AB}$=13.5 Hz, J$_{BX}$=76.2 Hz, 1H), 4.44–4.54 (AB, J$_{AB}$=13.4 Hz), 4.96–5.05 (m, 1H), 7.21–7.31 (m, 5H); 13C NMR (90 MHz, CDCl$_3$), 19.47, 28.28, 42.35, 63.91, 76.70, 82.79, 126.92, 128.74, 128.78, 137.30, 154.59, 166.86. EM Anal. Calcd Cl$_6$H$_{22}$O$_5$: C, 65.29; H, 7.53. Found: C, 65.33; H, 7.56.

EXAMPLE 5

Preparation of Carbonate A5

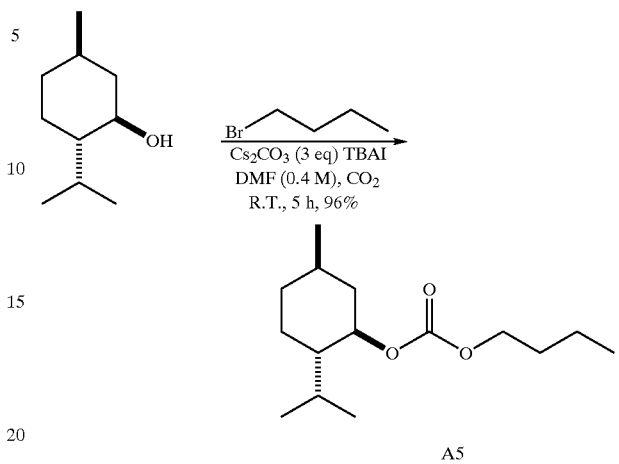

To a solution of L-(−)-menthol (200mg, 1.28 mmol) in anhydrous N,N-dimethylformamide (3.2 mL, 0.4 M), are added cesium carbonate (1.25 g, 3.84 mmol, 3 eq) and tetrabutylammonium iodide (400 mg, 1.28 mmol, 1 eq). Carbon dioxide gas is passed through the turbid mixture for a couple of minutes before 1-bromobutane (527 mg, 0.41 mL, 3.84 mmol, 1 eq) is introduced to the reaction mixture while stirring. Carbon dioxide continues to bubble through the reaction system at room temperature for 5 hours until all L-(−)-menthol is consumed. The reaction mixture is quenched, poured into DI water (30 mL) and extracted thoroughly by 3:1 hexanes-EtOAc (60 mL). The resulting organic layer is washed with DI water (2' 30 mL), saturated brine (30 mL) and dried over anhydrous sodium sulfate. The solvent is evaporated by vacuum and the remaining residue is subjected to flash column chromatography (9:1 hexanes-EtOAc). A clear oil is obtained as desired carbonate A5 (316 mg, 96%): $R_f$ 0.51 (9:1 hexanes-EtOAc); IR (thin film) 2962, 2931, 2875, 1749, 1460, 1394, 1262, 1183, 992, 953, 922, 793 cm$^{-1}$; $^1$H NMR (360 MHz, CDCl$_3$) 0.69–0.72 (d, J=4.9 Hz, 3H), 0.80–0.87(m, 10H), 0.94–0.97(m,2H), 1.28–1.35(m,4H), 1.54–1.61 (m, 4H), 1.86–1.92 (m, 1H), 1.92–1.99 (m, 1H), 4.03 (td, J=6.3 Hz, 1.1 Hz, 2H), 4.43 (td, J=10.8 Hz, 4.3 Hz, 1H); $^{13}$C NMR (90 MHz, CDCl$_3$) 13.2, 15.8, 18.5, 20.3, 21.6, 22.9, 25.7, 30.3, 31.2, 33.8, 40.4, 46.6, 67.1, 77.7, 154.6. EM Anal. Calcd. C$_{15}$H$_{28}$O$_3$: C, 70.27; H, 11.01. Found: C, 70.32; H, 10.94.

EXAMPLE 6

Preparation of Carbonate A14

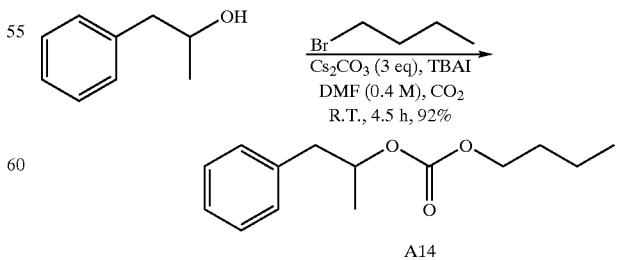

1-Phenyl-2-propanol (100 mg, 0.74 mmol) is dissolved in anhydrous N,N-dimethylformamide (1.9 mL) to make a 0.4

M solution. Then, cesium carbonate (719 mg, 2.22 mmol, 3 eq) and tetrabutylammonium iodide (230 mg, 0.74 mmol, 1 eq) are added to the solution while stirring. After carbon dioxide is passed through the suspension for a couple of minutes, 1-bromobutane (304 mg, 0.24 mL, 2.2 mmol) is injected into the reaction mixture. Carbon dioxide is bubbled continuously through the reaction at ambient temperature for a period of 4.5 hours and all the starting material, 1-phenyl-2-propanol, is consumed. The reaction mixture was then taken up by 3:1 hexanes-EtOAc (60 mL), washed with DI water (3' 30 mL) and brine (30 mL), and dried over anhydrous sodium sulfate. The resulting organic layer is filtered, removed of solvent and committed to flash column chromatography (9:1 hexanes-EtOAc). Desired carbonate A14 is obtained in good yield (160 mg, 92%) as a clear oil: $R_f$ 0.47 (9:1 hexanes-EtOAc); IR (thin film) 3092, 3065, 3032, 2967, 2941, 2875, 1743, 1460, 1395, 1262, 1137, 1062, 933, 795, 752, 703 cm$^{-1}$; $^1$H NMR (360 MHz, CDCl$_3$) 0.93–0.98 (t, J=7.3 Hz, 3H), 1.28–1.31 (d, J=6.3 Hz, 3H), 2H), 1.60–1.69 (m, 2H), 2.80 (A$\underline{B}$X, $J_{AB}$=13.5 Hz, $J_{AX}$=6.9 Hz, 1H), 3.04 (A$\underline{B}$X, $J_{AB}$=13.5 Hz, $J_{AB}$=6.5 Hz, 1H), 4.09–4.14 (t,J=6.6 Hz, 2H), 4.97–5.03 (m, 1H), 7.22–7.34 (m, 5H); $^{13}$C NMR (90 MHz, CDCl$_3$) 13.78, 19.04, 19.51, 30.81, 42.42, 67.70, 75.57, 126.68, 128.52, 128.57, 137.39, 154.92. EM Anal. Calcd. $C_{14}H_{20}O_3$: C, 71.16; H, 8.53. Found: C, 72.20; H, 8.57.

EXAMPLE 7

Preparation of Carbonate A7

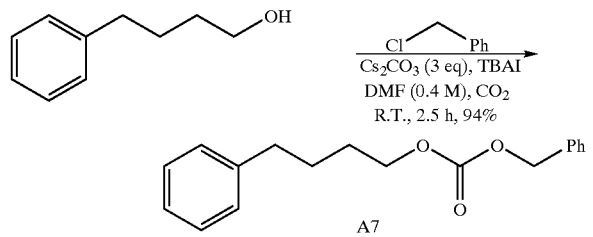

Into a solution of 4-phenyl-1-butanol (100 mg, 0.67 mmol) in anhydrous N,N-20 dimethylformamide (1.6 mL, 0.4 M), are added tetrabutylammonium iodide (208 mg, 0,67 mmol, 1 eq) and cesium carbonate (652 mg, 2.01 mmol, 3 eq) under the protection of nitrogen. After carbon dioxide gas is passed through the suspension for a couple of minutes, benzyl chloride (255 mg, 0.25 mL, 2.01 mmol, 3 eq) is introduced to the reaction mixture. The reaction is allowed to proceed at room temperature for a period of two and a half hours with carbon dioxide bubbling through the reaction and all the starting material, 4-phenyl-1-butanol, is consumed. The reaction is quenched, poured into DI water (30 mL) and extracted thoroughly with 3:1 hexanes-EtOAc (60 mL). The resulting organic layer is washed successively with DI water (2' 30 mL), saturated brine (30 mL) and dried over anhydrous sodium sulfate. Filtration and removal of solvent in vacuo provides a yellowish crude oil, which is purified by flash column chromatography (30:1 hexanes-EtOAc) to yield carbonate A7 (177 mg, 94%) as a clear oily liquid: $R_f$ 0.42 (9:1 hexanes-EtOAc); IR (neat film) 3098, 3067, 3035, 2948, 1748, 1610, 1492, 1459, 1376, 1263, 796, 758, 701 cm$^{-1}$; $^1$H NMR (360 MHz, CDCl$_3$) 1.72–1.80 (m, 4H), 2.66–2.71 (m, 2H), 4.18–4.27 (m, 2H), 5.20–7.22–7.45 (m,10H); $^{13}$C NMR (90 MHz, CDCl$_3$) 27.60, 28.35, 35.50, 68.11, 69.57, 125.96, 128.45, 128.51, 128.60, 128.69, 135.46, 141.99, 155.34. EM Anal. Calcd. $C_{18}H_{20}O_3$: C, 76.03; H, 7.09. Found: C, 76.11; H, 7.07.

EXAMPLE 8

Preparation of Carbonate A8

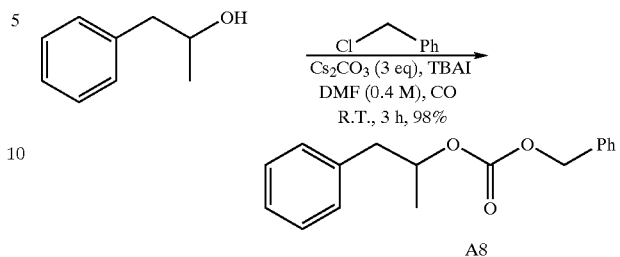

Under an atmosphere of nitrogen, 1-phenyl-2-propanol (100 mg, 0.74 mmol) is dissolved in anhydrous N,N-dimethylformamide (1.9 mL, 0.4 M). Tetrabutylammonium iodide (230 mg, 0.74 mmol, 1 eq) and cesium carbonate (719 mg, 2.22 mmol, 3 eq) are added into the solution while stirring. Carbon dioxide is passed through the suspension for a couple of minutes to saturate the DMF solution, before benzyl chloride (282 mg, 0.26 mL, 2.22 mmol, 3 eq) is added to the reaction mixture. Carbon dioxide gas is bubbled through the turbid mixture for a period of three hours at ambient temperature until all 1-phenyl-2-propanol is consumed in the reaction. Deionized water (1 mL) is injected into the reaction mixture to quench the reaction and the misty mixture is taken up by 3:1 hexanes-EtOAc (60 mL). The organic layer is washed successively with DI water (3' 30 mL), brine (30 mL) and is dried over anhydrous sodium sulfate. Solvent is removed in uacuo, and the residue is subjected to flash column chromatography (30:1 hexanes-EtOAc) to afford pure cabonate A8 (194mg, 98%) as a colorless liquid: $R_f$ 0.27 (15:1 hexanes-EtOAc); IR (thin film) 3086, 3067, 3035, 2985, 2940, 1748, 1603, 1502, 1458, 1383, 1263, 1137, 1048, 916, 790, 752, 701 cm$^{-1}$; $^1$H NMR (360 MHz, CDCl$_3$) 1.28–1.31 (d, J=6.3 Hz, 3H), 2.80 (A$\underline{B}$X, $J_{AB}$=13.6 Hz, $J_{AX}$=6.8 Hz, 1H), 3.03 ($\underline{A}$BX, $J_{AB}$=13.6 Hz, $J_{bX}$=6.5 Hz, 1H), 4.98–5.05 (m, 1H), 5.13 (s, 2H), 7.20–7.39 (m, 5H); $^{13}$C NMR (90 MHz, CDCl$_3$) 19.51,42.36, 69.39, 75.98, 126.72, 128.32, 128.53, 128.55, 128.68, 129.58, 135.58, 137.29, 154.76.

EXAMPLE 9

Preparation of Carbonate A15

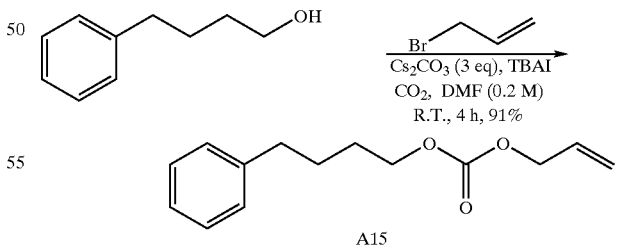

Into a solution of 4-phenyl-1-butanol (100 mg, 0.67 mmol) in anhydrous N,N-dimethylformamide (3.2 mL, 0.2 M), are added tetrabutylammonium iodide (208 mg, 0.67 mmol, 1 eq) and cesium carbonate (651 mg, 2.01 mmol, 3 eq) under the protection of nitrogen. After carbon dioxide is bubbled through the reaction mixture for a couple of minutes to saturate the solution, allyl bromide (243 mg, 0.17 mL, 2.01 mmol, 3 eq) is introduced. The reaction is allowed to proceed for about four hours at room temperature with carbon dioxide gas passing through the reaction mixture. The reaction is quenched, poured into DI water (30 mL) and extracted with 3:1 hexanes-EtOAc(60 mL). The organic layer is then washed with deionized water (2' 30 mL) and dried over anhydrous sodium sulfate. Filtration and removal of solvent in vacuo provides a crude oil, which is purified by flash column chromatography (15:1 hexanes-EtOAc) to yield 142 mg desired carbonate A15 (91%) as a clear oily liquid: $R_f$=0.32 (15:1 hexanes-EtOAc); IR (thin film) 3086, 3064, 3033, 2947, 2861, 1743, 1654, 1604, 1496, 1453, 1394, 1256, 796, 748, 703 cm$^{-1}$; $^1$H NMR (360 MHz, CDCl$_3$) 1.60–1.74 (m, 4H), 2.65–2.67 (m, 2H), 4.18–4.20 (m, 2H), 4.62–4.64 (d, J=5.8 Hz, 2H), 5.26–5.30 (d J=10.4 Hz, 1H), 5.35–5.40 (d, J=17.2 Hz, 1H), 5.90–6.01 (ddt, J=16.2 Hz, 11.4 Hz, 6.6 Hz, 1H), 7.18–7.32 (m, 5H); $^{13}$C NMR (90 MHz, CDCl$_3$) 27.19, 27.96, 35.10, 67.66, 68.03, 118.55, 125.56, 128.05, 128.10, 131.36, 141.60, 154.79. EM Anal. Calcd. $C_{14}H_{18}O_3$: C, 71.77; H, 7.74. Found: C, 71.81; H, 7.76.

EXAMPLE 10

Preparation of Methyl Mandelate Benzyl Carbonate

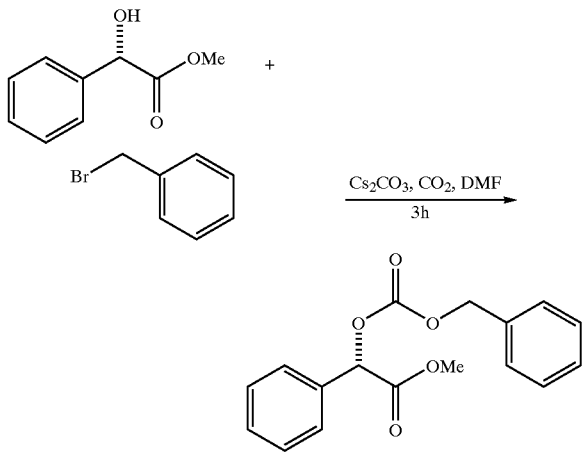

Methyl (S)-(+)-mandelate (332 mg, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before benzyl bromide (0.71 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 390 mg of the desired methyl mandelate benzyl carbonate (65%): IR (thin film) 3004, 2956, 2839, 1748, 1613, 1516, 1455, 1383, 1246, 1175, 1115, 1027, 953, 824,789 cm$^{-1}$; $^1$H NMR (360 MHz, CDCl$_3$) d 3.72 (s, 3 H), 5.20 (s, 2 H), 5.86 (s, 1 H), 7.3~7.5 (m, 10 H); $^{13}$C NMR (90 MHz, CDCl$_3$) d 52.65, 71.17, 127.53, 128.31, 128.51, 128.56, 128.73, 129.38, 133.07, 134.69, 154.31, 168.91.

EXAMPLE 11

Preparation of Methyl Mandelate Benzyl Carbonate

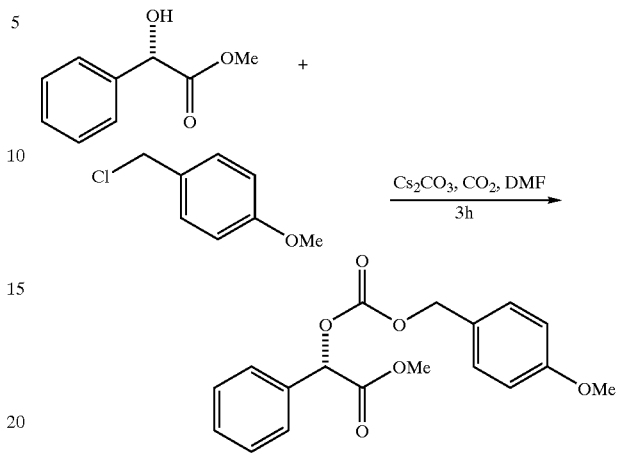

Methyl (S)-(+)-mandelate (332 mg, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before 4-methoxybenzyl chloride (0.81 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 607 mg of the desired methyl mandelate benzyl carbonate (92%): IR (thin film) 3036, 2957, 2838, 1748, 1614, 1517, 1456, 1383, 1246, 1175, 1028, 928, 824 cm$^{-1}$; $^1$H NMR (360 MHz, CDCl$_3$) d 3.73 (s, 3H), 3.79 (s, 3H), 5.16 (s, 2 H), 5.88 (s, 1H), 6.88–7.48 (m, 9 H); $^{13}$C NMR (90 MHz, CDCl$_3$) d 52.57, 55.11, 70.04, 113.81, 127.47, 128.67, 129.30, 130.26, 133.10, 154.27, 159.83, 168.90. EM Anal. Calcd. $C_{18}H_{18}O_6$: C, 65.45; H, 5.49. Found: C, 65.51; H, 5.55.

EXAMPLE 12

Preparation of Pantolactone Benzyl Carbonate

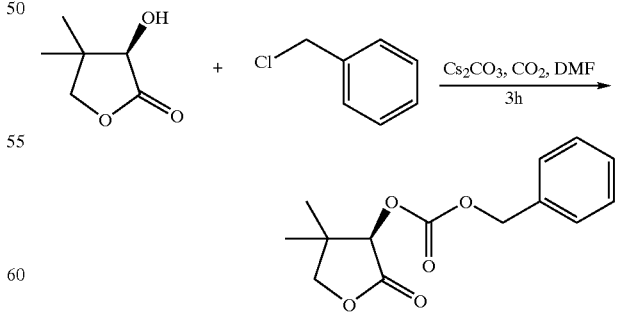

(R)-Pantolactone (260 mg, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before benzyl chloride (0.69 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 475 mg of the desired pantolactone benzyl carbonate (90%): IR (thin film) 2965, 2932, 1790, 1455, 1121, 1007, 740, 699, 558 cm$^{-1}$; $^1$H NMR (360 MHz, CDCl$_3$) d 1.08 (s, 3 H), 1.18 (s, 3H), 3.97–3.99 (AB, J=9.07 Hz), 5.14 (s, 1 H), 5.19 (s, 1 H), 7.32–$^{13}$C NMR (90 MHz, CDCl$_3$) d 19.58, 22.76, 39.98, 70.54, 75.95, 78.43, 128.58, 128.63, 128.69, 134.43, 154.30, 171.64.

EXAMPLE 13

Preparation of Pantolactone 4-methoxy Benzyl Carbonate

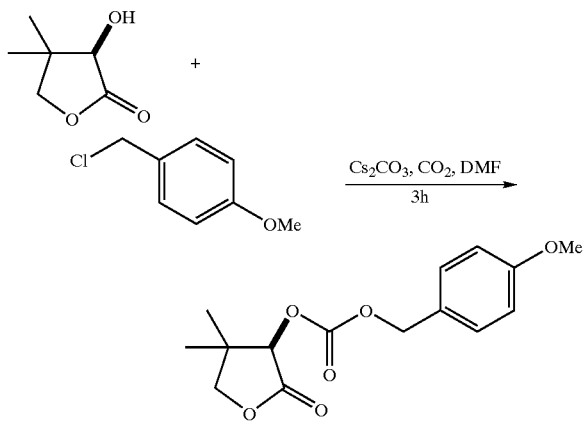

(R)-Pantolactone (260 mg, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before 4-methoxybenzyl chloride (0.81 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 553 mg of the desired pantolactone 4-methoxybenzyl carbonate (94%): IR (thin film) 2967, 1798, 1753, 1613, 1516, 1465, 1381, 1246, 1175, 1131, 1022, 824 cm$^{-1}$; $^1$H NMR (360 MHz, CDCl$_3$) d 1.06 (s, 3 H), 1.20 (s, 3H), 3.75 (s, 3H), 3.95–3.98 (AB, J=9.04 Hz), 5.12 (s, 1H), 6.85 (d, 2H, J=8.6 Hz), 7.29 (d, 2H, J=8.6 Hz); $^{13}$C NMR CDCl$_3$) d 19.57, 22.77, 39.97, 55.19, 70.48, 75.96, 78.34, 113.93, 126.53, 130.37, 154.31, 159.96, 171.68. EM Anal. Calcd. C$_{15}$H$_{18}$O$_6$: C, 61.22; H, 6.16. Found: C, 61.47; H, 6.17.

EXAMPLE 14

Preparation of Ethyl Lactate Benzyl Carbonate

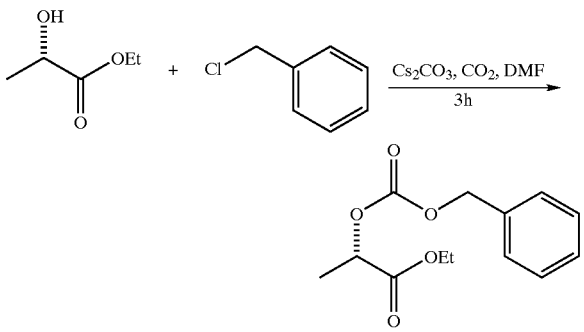

Ethyl (S)-lactate (0.23 mL, 2 mmol) is dissolved in anhydrous N,N-dimethylforamide (8 mL), and powdered cesium carbonate (1.95 g, 6 nmol, 3 eq) is added. The suspension is then stirred at room temperature while passing carbon dioxide gas for 1 hour before benzyl chloride (0.69 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 454 mg of the desired ethyl lactatebenzyl carbonate (90%): IR(thinfilm) 2988, 2942, 1748, 1456, 1383, 1266, 1207, 1136, 1075, 1028, 918, 789, 753, 698 cm$^{-1}$; $^1$HNMR(360 MHz, CDCl$_3$) d 1.19 (t, 3H, J=7.13 Hz), 1.46 (d, 3H, J=7.06 Hz), 4.15 (q, 2H, J=4.49 (q, 1H, J=7.08 Hz), 5.13 (s, 2H), 7.26–7.32 (m, 5H); $^{13}$C NMR (90 MHz, CDCl$_3$) d 13.82, 16.72, 61.27, 69.69, 71.60, 128.09, 128.14, 128.30, 128.35, 128.40, 134.82, 154.27, 170.15.

EXAMPLE 15

Preparation of Ethyl Lactate 4-methoxybenzyl Carbonate

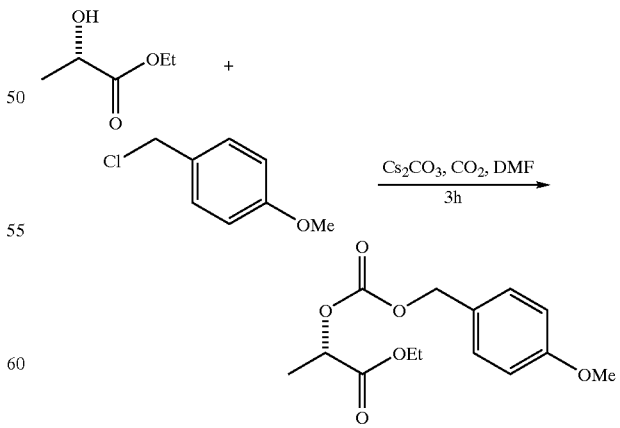

Ethyl (S)-lactate (0.23 mL, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before 4-methoxybenzyl chloride (0.81 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 530 mg of the desired ethyl lactate 4-methoxybenzyl carbonate (94%): IR (thin film) 2987, 2839, 1748, 1613, 1516, 1456, 1383, 1248, 1205, 1135, 1074, 1032, 921, 823, 790 cm$^{-1}$; $^1$H NMR (360 MHz, CDCl$_3$) d 1.20 (t, 3H, J=7.13 Hz), 1.45 (d, 3H, J=7.09 Hz), 3.76 (s, 3H), 4.16 (q, 2H, J=7.13 Hz), 4.94 (q, 1H, J=7.06 Hz), 5.07 (s, 2H), 6.83 (d, 2H, J=8.50 Hz), 7.28 (d, 2H, J=8.43 Hz); $^{13}$C NMR (90 MHz, CDCl$_3$) d 13.95, 16.86, 61.41, 69.77, 71.64, 113.84, 127.00, 130.24, 154.40, 159.83, 170.36.

EXAMPLE 16

Preparation of Dimethyl Malate Benzyl Carbonate

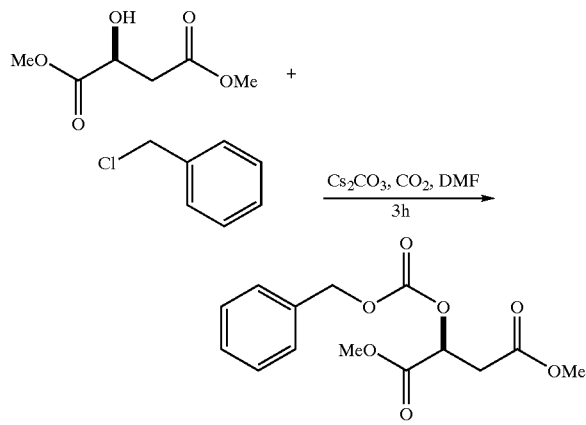

Dimethyl (S)-(−) malate (0.27 mL, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before benzyl chloride (0.69 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 384 mg of the desired dimethyl malate benzyl carbonate (65%): IR (thin film) 3034, 2957, 1746, 1439, 1383, 1216, 1042, 909, 756, 699 cm$^{-1}$; $^1$H NMR (360 MHz, CDCl$_3$) d 2.93 (d, 2H, J=6.26 Hz), 3.71 (s, 3H), 3.78 (s, 3H), 5.22 (s, 2H, J=6.08 Hz), 7.34–7.38 (m, 5H); $^{13}$C NMR (90 MHz, CDCl$_3$) d 35.60, 51.97, 52.55, 70.00, 71.13, 128.17, 128.43, 153.94, 168.80, 169.10.

EXAMPLE 17

Preparation of Benzyl Carbonate

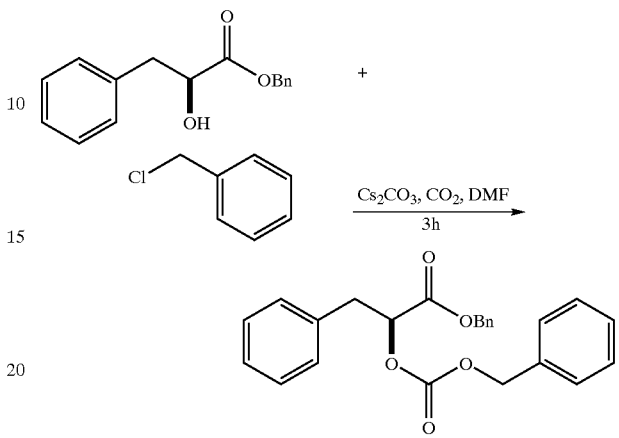

Benzyl 2-(S)-hydroxy-3-phenyl propionate (510 mg, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas for 1 hour before benzyl chloride (0.69 mL, 6 mmol, 3 eq) is added to the solution. Carbon dioxide gas is continuously bubbled through the solution for another 2~3 hours until the starting material is consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 663 mg of the desired benzyl carbonate (85%): IR (thin film) 3089, 3032, 2958, 1955, 1878, 1748, 1605, 1479, 1455, 1385, 1252, 1026, 908, 750, 697 cm$^{-1}$; $^1$H NMR (360 MHz, CDCl$_3$) d 3.17 (<u>A</u>BX, 1H, J$_{AB}$=14.3, J$_{AX}$=8.6 Hz), 3.18 (A<u>B</u>X, 1H, J$_{AB}$=14.3 Hz, J$_{BX}$=4.6 Hz), 5.14–5.19 (m, 4H), 5.21 (m, 1H), 7.19–7.34 (m, 15H); $^{13}$C NMR (90 MHz, CDCl$_3$) d 37.30, 67.17, 69.97, 76.09, 127.05, 128.20, 128.26, 128.31, 128.48, 128.52, 129.34, 134.79, 135.30, 154.45, 169.11.

EXAMPLE 18

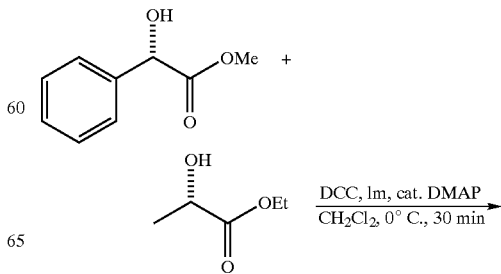

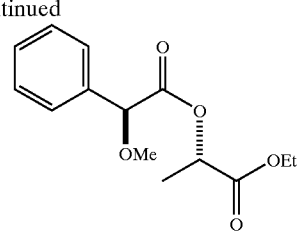

A solution of (S)-(+)-a-methoxyphenyl acetic acid (17 mg, 0.1 mmol), N,N-dicyclohexylcarbodiimide (DCC, 11 mg, 0.1 mmol), ethyl (S)-(−)-lactate (11 mL, 0.1 mmol), and a catalytic amount of DMAP in $CH_2Cl_2$ (2 mL) is allowed to stand at 0° C. for 30 minutes until esterification is complete. N,N-Dicyclohexylurea is filtered and the filtrate is concentrated in vacuo to provide crude oil, which is purified by column chromatography (3:1 hexanes-EtOAc) to afford the desired product (26 mg, 95%, 96% ee): IR (thin film) 2989, 2940, 2830, 1749, 1456, 1272, 1201, 1108, 735 cm$^{-1}$; $^1$H NMR (360 MHz, CDCl$_3$) d 1.23 (t, 3H, J=7.13 Hz), 1.42 (d, 2H, J=7.09 Hz), 3.45 (s, 3H), 4.18 (q, 2H, J=7.13 Hz), 4.87 (s, 1H), 5.08 (q, 1H, J=7.06 Hz), 7.34–7.48 (m, 5H); $^{13}$C NMR (90 MHz, CDCl$_3$) d 13.93, 16.65, 57.41, 61.39, 69.18, 82.18, 127.21, 128.51, 128.71, 135.85, 170.08, 170.25. EM Anal. Calcd. $C_{14}H_{18}O_5$: C, 63.15; H, 6.81. Found: C, 63.10; H, 6.87.

EXAMPLE 19

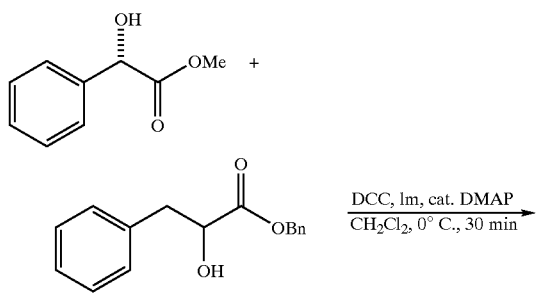

A solution of (S)-(+)-a-methoxyphenylacetic acid (17 mg, 0.1 mmol), N,N-dicyclohexylcarbodiimide (DCC, 11 mg, 0.1 mmol), benzyl 2-(S)-hydroxy-3-phenyl propionate (25 mg, 0.1 mmol), and a catalytic amount of DMAP in $CH_2Cl_2$(2 mL) is allowed to stand at 0° C. for 30 minutes until esterification is complete. N,N-Dicyclohexylurea is filtered and the filtrate is concentrated in vacuo to provide crude oil, which is purified by column chromatography (3:1 hexanes-EtOAc) to afford the desired product (37 mg, 93%, 97% ee): IR (thin film) 3031, 2931, 2829, 1750, 1479, 1455, 1276, 1169, 1112, 746, 698 cm$^{-1}$; $^1$H NMR (360 MHz, CDCl$_3$) d 3.06 (ABX, 1H, J$_{AB}$=14.3, J$_{AX}$=8.5 Hz), 3.10 (A BX, 1H, J$_{AB}$=14.3, J$_{BX}$=4.3Hz), 3.34 (s, 3H), 4.81 (s, 1H), 5.18 (s, 2H), 5.29(ABX, 1H), 6.93–7.35 (m, 5H); $^{13}$C NMR (90 MHz, CDCl$_3$) d 36.95, 57.39, 67.15, 73.24, 82.03, 126.78, 127.13, 128.27, 128.32, 128.38, 128.45, 128.49, 128.58, 129.09, 135.25, 135.66, 168.92, 170.03.

EXAMPLE 20

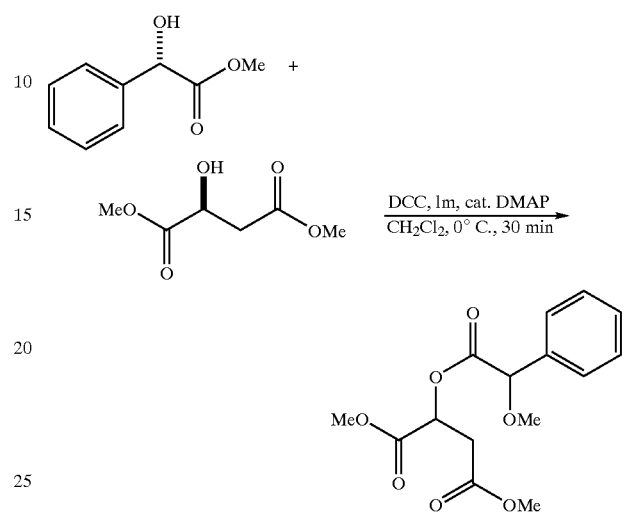

A solution of (S)-(+)-a-methoxyphenyl acetic acid (17 mg, 0.1 mmol), N,N-dicyclohexylcarbodiimide (DCC, 11 mg, 0.1 mmol), dimethyl (S)-(−)-malate (14 mL, 0.1 mmol), and a catalytic amount of DMAP in $CH_2Cl_2$ (2 mL) is allowed to stand at 0° C. for 30 minutes until esterification is complete. N,N-Dicyclohexylurea is filtered and the filtrate is concentrated in vacuo to provide crude oil, which is purified by column chromatography (3:1 hexanes-EtOAc) to afford the desired product (30 mg, 93%, 95% ee): IR (thin film) 3001, 2955, 2831, 1748, 1455, 1279, 1169, 1107, 1056, 955, 736 cm$^{-1}$; $^1$H NMR (360 MHz, CDCl$_3$) d 2.08 (d, 2H, J=6.90 Hz), 3.44 (s, 3H), 3.73 (s, 3H), 4.47 (s, 3H), 4.86 (s,1H), 5.50 (t, 1H, J=6.32 Hz), 7.33–7.43 (m, 5H); $^{13}$C NMR (90 MHz, CDCl$_3$) d 35.73, 51.93, 52.70, 57.45, 68.59, 82.01, 127.19, 128.52, 128.73, 135.69, 168.98, 169.62.

EXAMPLE 21

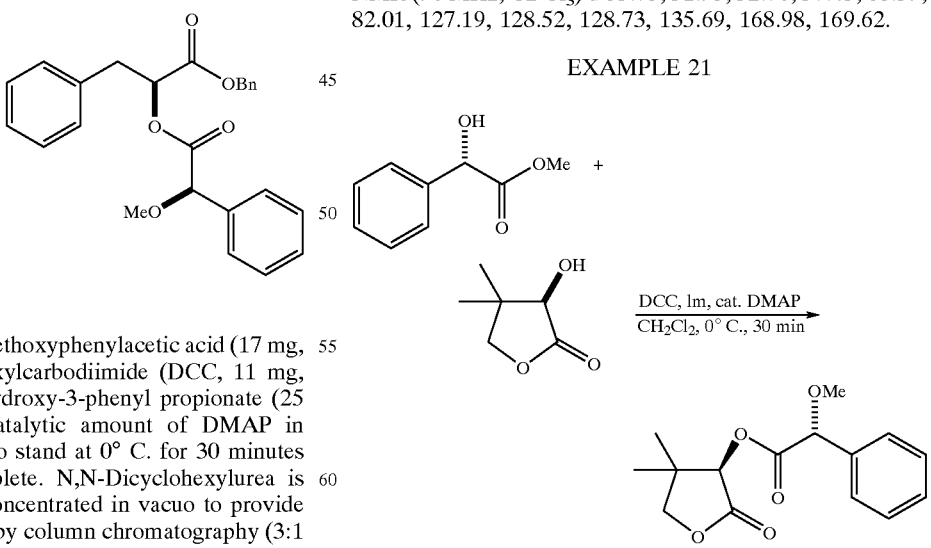

A solution of (S)-(+)-a-methoxyphenyl acetic acid (17 mg, 0.1 mmol), N,N-dicyclohexylcarbodiimide (DCC, 11 mg, 0.1 mmol), (R)-pantolactone (13 mg, 0.1 mmol), and a catalytic amount of DMAP in $CH_2Cl_2$ (2 mL) is allowed to stand at 0° C. for 30 minutes until esterification is complete. N,N-Dicyclohexylurea is filtered and the filtrate is concentrated in vacuo to provide crude oil, which is purified by column chromatography (3:1 hexanes-EtOAc) to afford the desired product (26 mg, 94%, 97% ee): IR (thin film) 2967, 2934, 2831, 1792, 1761, 1464, 1737, 1373, 1153, 955, 731 $cm^{-1}$; $^1H$ NMR (360 MHz, $CDCl_3$) d 1.05 (s, 3H), 1.13 (s, 3H), 3.49 (s, 3H), 3.98–4.02 (AB, 2H, J=9.02 Hz), 4.92 (s, 1H), 5.34 (s, 2H), 7.34–7.49 (m, 5H); $^{13}C$ NMR (90 MHz, $CDCl_3$) d 19.66, 22.85, 40.10, 57.50, 75.40, 76.62, 82.99, 126.89, 128.55, 128.85, 135.45, 169.94, 171.45. EM Anal. Calcd. $C_{15}H_{18}O_5$: C, 64.74; H, 6.52. Found: C, 64.46; H, 6.58.

EXAMPLE 22

Preparation of Cyclic Carbonate

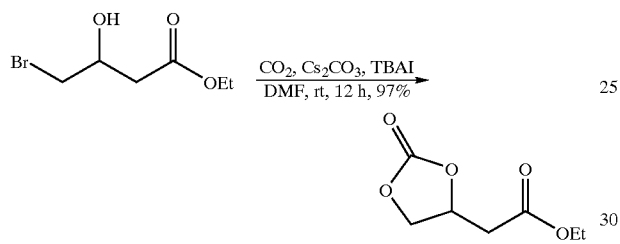

Ethyl 4-bromo-3-(S)-hydroxybutanoate (422 mg, 2 mmol) is dissolved in anhydrous N,N-dimethylforamide (8 mL), and powdered cesium carbonate (1.95 g, 6 mmol, 3 eq) is added. The suspension is then stirred at room temperature while passing carbon dioxide gas until the starting material was consumed. The reaction is quenched with water (20 mL) and extracted with EtOAc (3×20 mL). The resulting organic layer is washed consecutively with water (3×20 mL), brine (20 mL), and dried over anhydrous sodium sulfate. Filtration and concentration in vacuo provides an oil, which is purified by column chromatography (9:1 Hexanes-EtOAc) to yield 337 mg of the desired cyclic carbonate (97%): IR (thin film) 3475, 2985, 2937, 1810, 1739, 1404, 1333, 1265, 1179, 1079, 752 $cm^{-1}$; $^1H$ NMR (360 MHz, $CDCl_3$) d 1.28 (t, 3H, J=7.2 Hz), 2.76 (dd, 1H, J=16.85, 7.85 Hz), 2.94 (dd, 1, J=16.85, 5.40 Hz), 4.19 (tq, 3H, J=8.7, 7.2 Hz), 4.66 (t, 1H, J=8.7 Hz), 5.00–5.08 (m,1H); $^{13}C$ NMR (90 MHz, $CDCl_3$) d 14.00, 38.16, 61.42, 69.24, 72.40, 154.36, 168.91.

EXAMPLE 23

Merrifield Resin Bound Octyl Carbonate

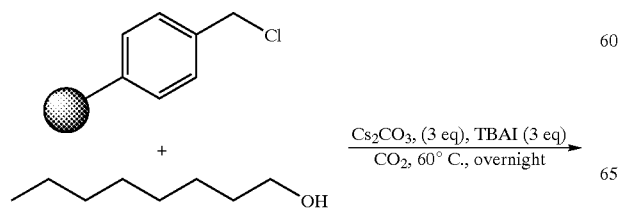

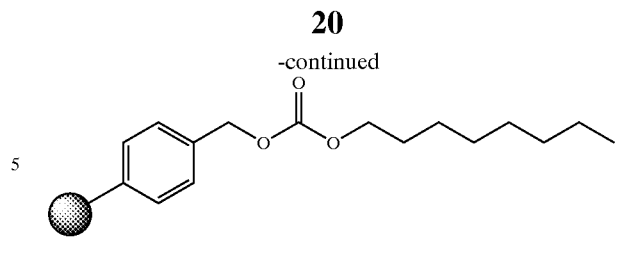

1-Octanol (781 mg, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with $MeOH/H_2O$, $H_2O$, 0.2NHCl, $H_2O$, THF, $CH_2Cl_2$, and MeOH. After drying under vacuum, 1.15 g of resin is obtained (54% yield): IR 3050, 3021, 2920, 2851, 1951, 1873, 1815, 1742, 1712, 1601, 1498, 1450, 1371, 1316, 771, 701, 545 $cm^{-1}$.

EXAMPLE 24

Merrifield Resin Bound Decyl Carbonate

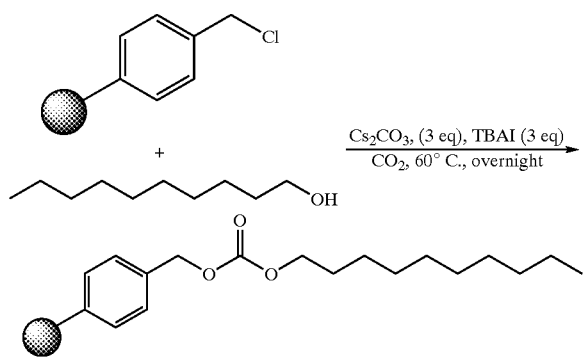

1-Decanol (1.14 mL, 6 mmol, 3 eq) is dissolved in anhydrous N,N-dimethylforamide (20 mL) to make a clear solution. Into the solution, are consecutively added cesium carbonate (1.95g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbled through the solution and the reaction is allowed to proceed overnight at 60° C. The mixture is then cooled to room temperature, and diluted with water. The resin is washed successively with $MeOH/H_2O$, $H_2O$, 0.2 N HCl, $H_2O$, THF, $CH_2Cl_2$, and MeOH. After drying under vacuum, 1.25 g of resin is obtained (77% yield): IR 3051, 3017, 2918, 2841, 1942, 1862, 1789, 1740, 1601, 1491, 1361, 763, 700, 544 $cm^{-1}$.

EXAMPLE 25

Merrifield Resin Bound Benzyl Carbonate

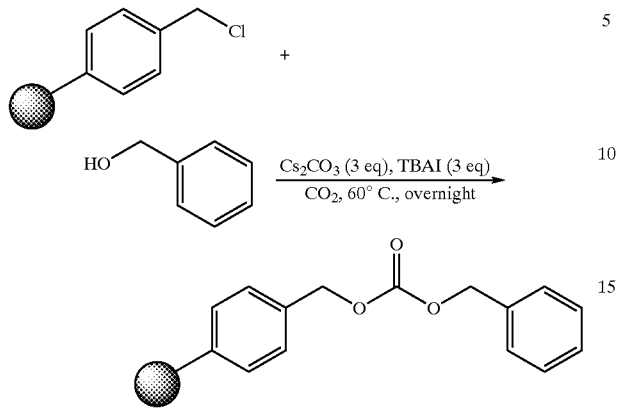

Benzyl alcohol (0.61 mL, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/$H_2O$, $H_2O$, 0.2 N HCl, $H_2O$, THF, $CH_2Cl_2$, and MeOH. After drying under vacuum, 1.22 g of resin is obtained (97% yield): IR 3061, 3020, 2918, 2851, 1945, 1870, 1816, 1744, 1605, 1499, 1448, 1361, 763, 698, 546 $cm^{-1}$.

EXAMPLE 26

Merrifield Resin Bound Benzyl 3-phenylpropyl Carbonate

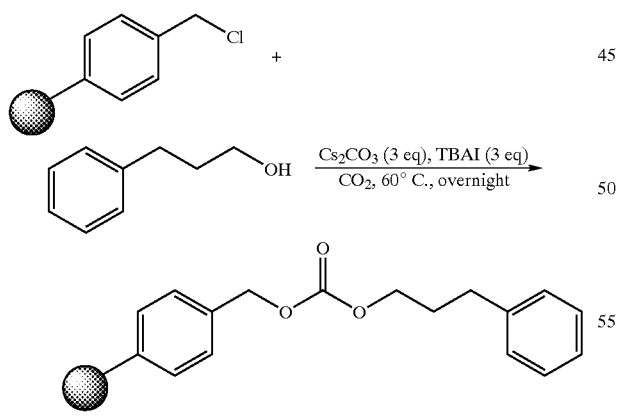

3-Phenylpropanol (0.81 mL, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/$H_2O$, $H_2O$, 0.2 N HCl, $H_2O$, THF, $CH_2Cl_2$, and MeOH. After drying under vacuum, 1.19 g of resin is obtained (65% yield): IR 3059, 3025, 2921, 2850, 1923, 1873, 1803, 1742, 1603, 1495, 1452, 1253, 759, 749 $cm^{-1}$.

EXAMPLE 27

Merrifield Resin Bound p-nitrobenzyl Carbonate

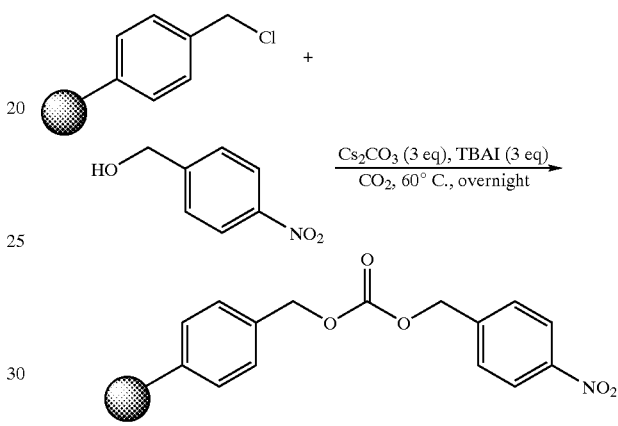

4-Nitro benzyl alcohol (920 mg, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/$H_2O$, $H_2O$, 0.2 N HCl, $H_2O$, THF, $CH_2Cl_2$, and MeOH. After drying under vacuum, 1.25 g of resin is obtained (77% yield): IR 3063, 3021, 2918, 2871, 1954, 1883, 1826, 1736, 1601, 1503, 1463, 1398, 1361, 1235, 961, 738 $cm^{-1}$.

EXAMPLE 28

Merrifield Resin Bound Cyclohexyl Carbonate

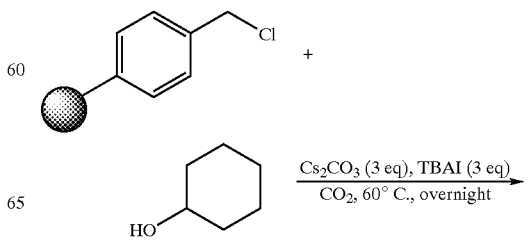

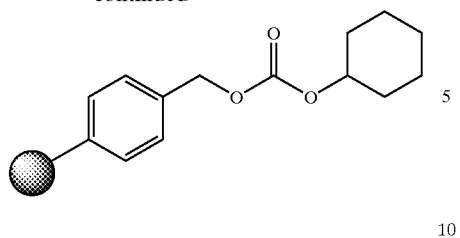

Cyclohexanol (0.63 mL, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.23 g of resin is obtained (98% yield): IR 3068, 3025, 2931, 2854, 1950, 1735, 1606, 1498, 1445, 1390, 1252, 1024, 934, 761, 696, 551 cm$^{-1}$.

EXAMPLE 29

Merrifield Resin Bound 3,3-dimethyl-2-butyl Carbonate

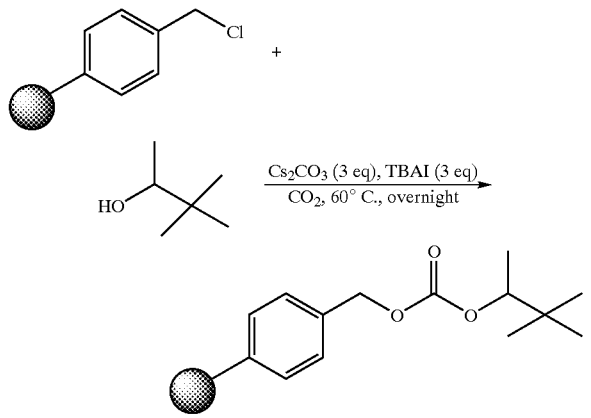

3,3-Dimethyl-2-butanol (0.76 mL, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.21 g of resin is obtained (98% yield): IR 3070, 3031, 2928, 1973, 1900, 1741, 1604, 1461, 1383, 1261, 1081, 931, 761, 700, 549 cm$^{1}$.

EXAMPLE 30

Merrifield Resin Bound Menthyl Carbonate

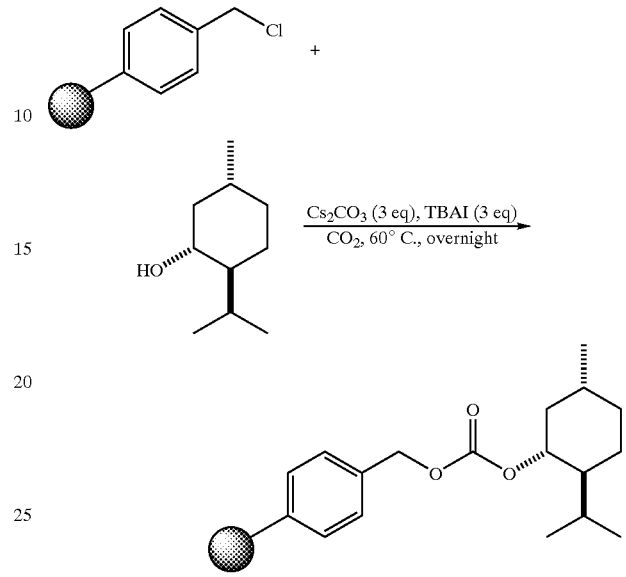

Menthol (938 mg, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.27 g of resin is obtained (83% yield): IR 3031, 2928, 2871, 1950, 18731, 1739, 1601, 1503, 1450, 1383, 1357, 956, 763, 701, 536 cm$^{-1}$.

EXAMPLE 31

Merrifield Resin Bound Methyl Mandelate Carbonate

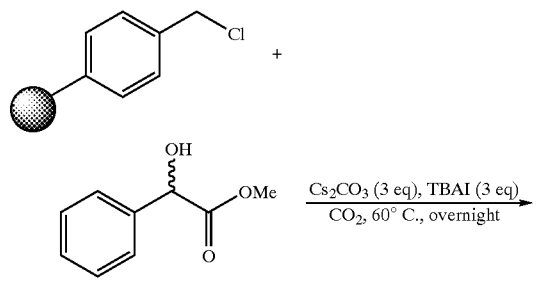

-continued

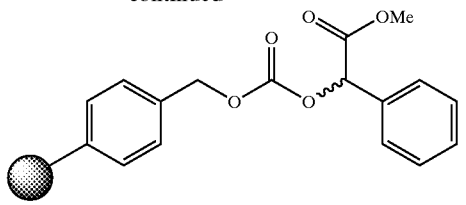

Methyl mandelate(1 g, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbled through the solution and the reaction is allowed to proceed overnight at 60° C. The mixture is then cooled to room temperature, and diluted with water. The resin is washed successively with MeOH/H$_2$O,H$_2$O, 0.2 N HCl, H$_2$O, THF, CH$_2$Cl$_2$, and MeOH. After drying under vacuum, 1.26 g of resin is obtained (76% yield): IR 3020, 2918, 2843, 1964, 1740, 1605, 1498, 1445, 1375, 1351, 1031, 771, 701, 551 cm$^{-1}$.

EXAMPLE 32

Merrifield Resin Bound Benzyl 3-phenylpropionate Carbonate

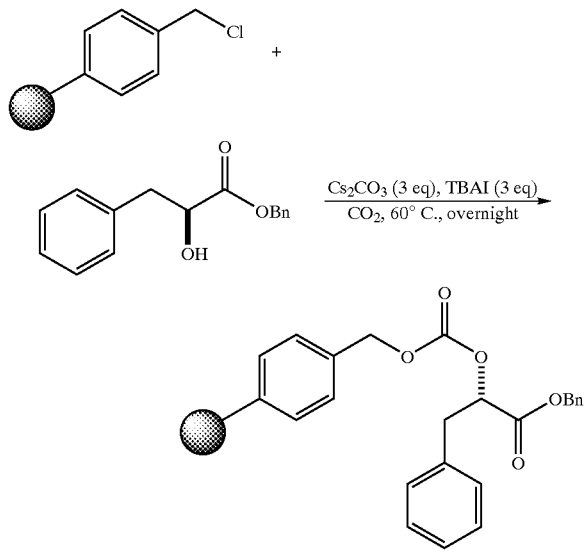

(S)-Benzyl 2-hydroxy-3-phenylpropionate (1.54 g, 6 mmol, 3 eq) is dissolved in anhydrous N,N-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the to solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.33 g of resin is obtained (63% yield): IR3071, 3035, 2921, 2846, 1943, 1874, 1611, 1495, 1462, 1394, 1253, 1172, 1036, 765, 700 cm$^{-1}$.

EXAMPLE 33

Merrifield Resin Bound Pantolactone Carbonate

Pantolactone (781 mg, 6 mmol, 3 eq) is dissolved in anhydrous NN-dimethylforamide (20 mL) to make a clear solution. Into the solution, are consecutively added cesium carbonate (1.95 g, 6 mmol) and tetrabutylammonium iodide (2.22 g, 6 mmol, 3 eq). The suspension is stirred at room temperature while passing carbon dioxide gas through for 1 hour before Merrifield's peptide resin (1 g, 2 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.16 g of resin is obtained (58% yield): IR 3068, 3031, 2963, 2932, 1983, 1900, 1749, 1610, 1501, 1461, 1387, 1251, 1024, 824, 750, 698, 541 cm$^{-1}$.

EXAMPLE 34

Wang Resin Bound Octyl Carbonate

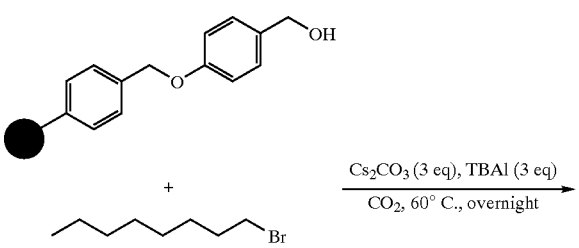

-continued

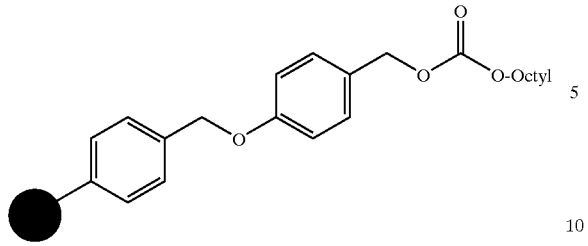

Wang resin (1. g, 1.5 mmol) is dissolved in anhydrous N,N-dimethylforamide (20 mL) to make a suspension. Into the solution, are consecutively added cesium carbonate (1.47 g, 4.5 mmol, 3 eq) and tetrabutylammonium iodide (1.66 g, 4.5 mmol, 3 eq). The suspension is stirred at room temperature while passing carbon dioxide gas through for 1 hour before 1-bromooctane (0.78 mL, 4.5 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.30 g of resin is obtained (97% yield): IR 3061, 3034, 2931, 2854, 1953, 1894, 1741, 1606, 1507, 1468, 1249, 1176, 1015, 951, 843, 774, 700, 543 cm$^{-1}$.

EXAMPLE 35

Wang Resin Bound Decyl Carbonate

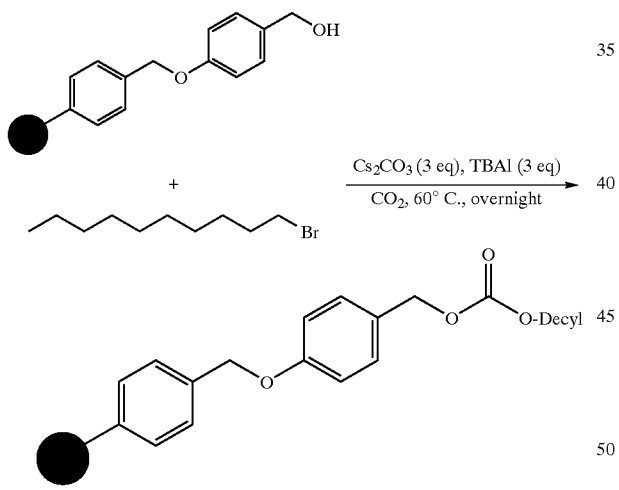

Wang resin (1. g, 1.5 mmol) is dissolved in anhydrous N,N-dimethylforamide (20 mL) to make a suspension. Into the solution, were consecutively added cesium carbonate (1.47 g, 4.5 mmol, 3 eq) and tetrabutylammonium iodide (1.66 g, 4.5 mmol, 3 eq). The suspension is stirred at room temperature while passing carbon dioxide gas through for 1 hour before 1-bromodecane (1.25 mL, 4.5 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.37 g of resin is obtained (99% yield): IR 3071, 3042, 2934, 2853, 1971, 1894, 1743, 1603, 1508, 1462, 1249, 1171, 1023, 833, 764, 701, 547 cm$^{-1}$.

EXAMPLE 36

Wang Resin Bound Benzyl Carbonate

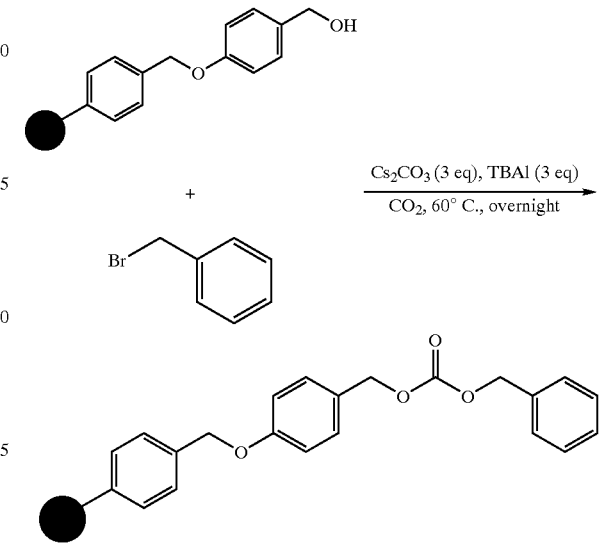

Wang resin (1. g, 1.5 mmol) is dissolved in anhydrous N,N-dimethylforamide (20 mL) to make a suspension. Into the solution, are consecutively added cesium carbonate (1.47 g, 4.5 mmol, 3 eq) and tetrabutylammonium iodide (1.66 g, 4.5 mmol, 3 eq). The suspension is stirred at room temperature while passing carbon dioxide gas through for 1 hour before benzyl bromide (0.71 mL, 4.5 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/H$_2$O, H$_2$O, 0.2 N HCl, H$_2$O, THF, CH$_2$Cl$_2$, and MeOH. After drying under vacuum, 1.25 g of resin is obtained (91% yield): IR 3080, 3032, 2931, 1951, 1881, 1745, 1614, 1506, 1543, 1400, 1243, 1031, 841, 763, 552 cm$^{-1}$.

EXAMPLE 37

Wang Resin Bound p-nitrobenzyl Carbonate

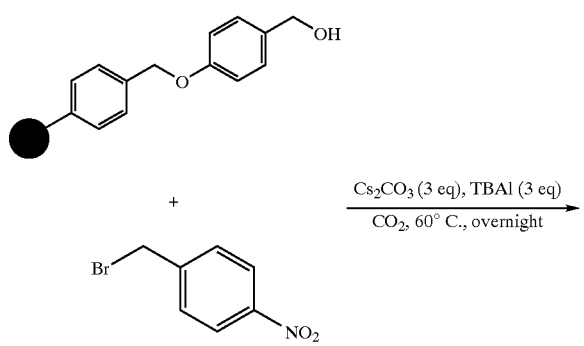

-continued

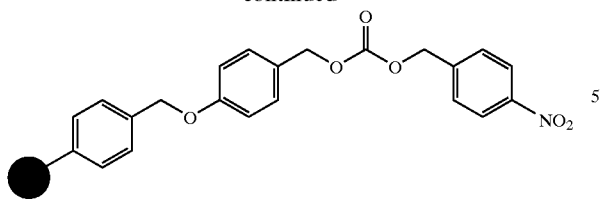

Wang resin (1. g, 1.5 mmol) is dissolved in anhydrous N,N-dimethylforamide (20 mL) to make a suspension. Into the solution, are consecutively added cesium carbonate (1.47 g, 4.5 mmol, 3 eq) and tetrabutylammonium iodide (1.66 g, 4.5 mmol, 3 eq). The suspension is stirred at room temperature while passing carbon dioxide gas through for 1 hour before p-nitro benzyl (1.03 g, 4.5 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/$H_2O$, $H_2O$, 0.2 N HCl, $H_2O$, THF, $CH_2Cl_2$, and MeOH. After drying under vacuum, 1.30 g of resin is obtained (83% yield): IR 3070, 3031, 2924, 1954, 1877, 1746, 1605, 1461, 1246, 1178, 1034, 837, 771, 701, 541 $cm^{-1}$.

EXAMPLE 38

Wang Resin Bound p-methoxybenzyl Carbonate

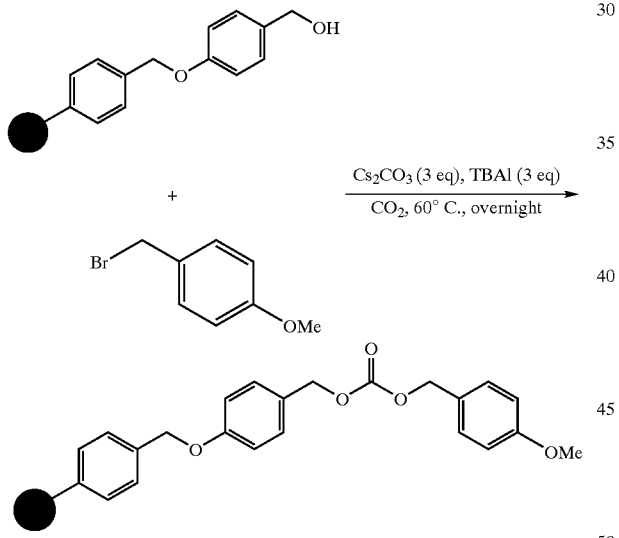

Wang resin (1. g, 1.5 mmol) is dissolved in anhydrous N,N-dimethylforamide (20 mL) to make a suspension. Into the solution, are consecutively added cesium carbonate (1.47 g, 4.5 mmol, 3 eq) and tetrabutylammonium iodide (1.66 g, 4.5 mmol, 3 eq). The suspension is stirred at room temperature while passing carbon dioxide gas through for 1 hour before p-nitro benzyl (0.81 mL, 4.5 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/$H_2O$, $H_2O$, 0.2 N HCl, $H_2O$, THF, $CH_2Cl_2$, and MeOH. After drying under vacuum, 1.27 g of resin is obtained (83% yield): IR 3065, 3031, 2931, 1951, 1882, 1740, 1605, 1461, 1398, 1247, 1008, 821, 761, 700, 551 $cm^{-1}$.

EXAMPLE 39

Wang Resin Bound Isopropyl Carbonate

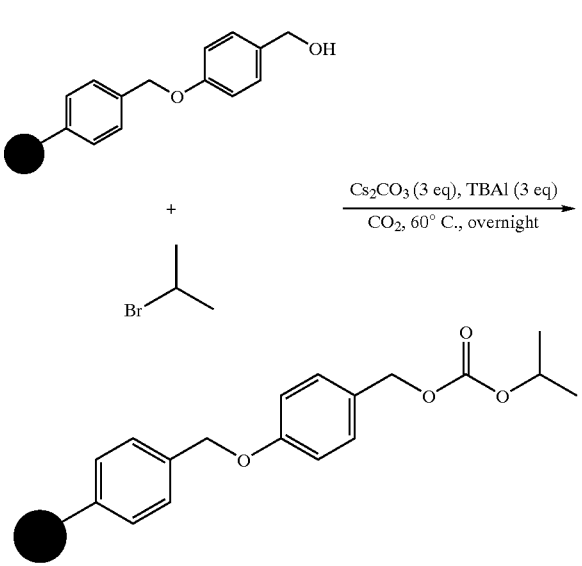

Wang resin (1. g, 1.5 mmol) is dissolved in anhydrous N,N-dimethylforamide (20 mL) to make a suspension. Into the solution, are consecutively added cesium carbonate (1.47 g, 4.5 mmol, 3 eq) and tetrabutylammonium iodide (1.66 g, 4.5 mmol, 3 eq). The suspension is stirred at room temperature while passing carbon dioxide gas through for 1 hour before isopropyl bromide (0.56 mL, 4.5 mmol) is added to the solution. Carbon dioxide gas continuously bubbles through the solution and the reaction is allowed to proceed overnight at 60° C. The mixture is then cooled to room temperature, and diluted with water. The resin is washed successively with MeOH/$H_2O$, $H_2O$, 0.2 N HCl, $H_2O$, THF, $CH_2Cl_2$, and MeOH. After drying under vacuum, 1.05 g of resin is obtained (28% yield): IR 3071, 3034, 2921, 1968, 1818, 1738, 1604, 1467, 1391, 1245, 1012, 883, 765, 698, 550 $cm^{-1}$.

EXAMPLE 40

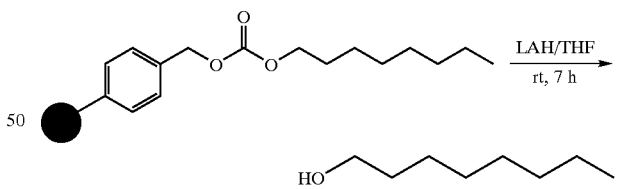

A dry 50 mL round bottomed flask, equipped with a magnetic stirring bar, is charged with 20 mL of THF and 1 g (1 mmol) of carbonate resin under an atmosphere of nitrogen. The suspension is cooled to 0° C., and 113 mg (3 mmol) of lithium aluminum hydride. The mixture is stirred for 7 hours at room temperature and cooled again to 0° C. This mixture is carefully worked up by the dropwise and sequential addition of 0.1 mL of water, 0.1 mL of 15% aqueous sodium hydroxide solution, and an additional 0.34 mL of water. The reaction mixture is filtered through a coarse filtration fritted glass to remove aluminum salts and the latter were washed four times with 10 mL of diethyl ether. The combined filtrates and washings were dried over magnesium sulfate and concentrated under reduce pressure. The crude product is purified using flash chromatography to provide 130 mg (quantitative yield) of 1-octanol.

EXAMPLE 41

Preparation of p-nitrobenzyl Alcohol

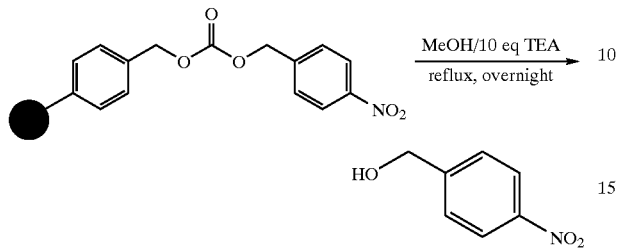

A 50 mL round bottomed flask, equipped with a magnetic stirring bar and a reflux condenser, is charged with 20 mL of methanol and 1 g (1.5 mmol) of carbonate resin and 10 equivalents of triethylamine. The mixture is heated at reflux for overnight and then cooled to room temperature. The reaction mixture is filtered through a coarse filtration fritted glass to remove the resin and the latter are washed four times with 10 mL of methanol. The combined filtrates and washings are dried over magnesium sulfate and concentrated under reduce pressure. The crude product is purified using flash chromatography to provide 210 mg (91%) of p-nitrobenzyl alcohol: $^1$H NMR (360 MHz, CDCl$_3$) d 1.89 (s, 1H), 4.76 (s, 3H), 7.46 (d, 2H, J=8.2 Hz), 8.14 (d, 2H, J=8.2 Hz).

EXAMPLE 42

Preparation of p-nitrobenzyl Alcohol

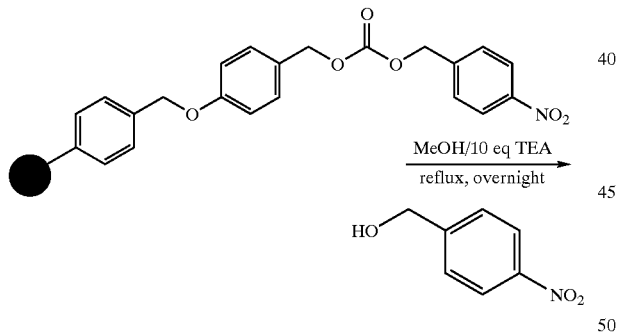

A 50 mL round bottomed flask, equipped with a magnetic stirring bar and a reflux condenser, is charged with 20 mL of methanol and 1 g (1 mmol) of carbonate resin and 10 equivalents of triethylamine. The mixture is heated at reflux for overnight and then cooled to room temperature. The reaction mixture is filtered through a coarse filtration flitted glass to remove the resin and the latter is washed four times with 10 mL of methanol. The combined filtrates and washings are dried over magnesium sulfate and concentrated under reduce pressure. The crude product is purified using flash chromatography to provide 141 mg (92%) of p-nitrobenzyl alcohol: $^1$H NMR (360 MHz, CDCl$_3$) d 1.89 (s, 1H), 4.76 (s, 3H), 7.46 (d, 2H, J=8.2 Hz), 8.14 (d, 2H, J=8.2 Hz).

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

What is claimed is:

1. A protocol for carbonate synthesis comprising:
   ligating an organic alcohol to an organic electrophile in the presence of a cesium base, and at a temperature less than 80° C., to form a carbonate.
2. The protocol of claim 1, wherein said ligating is in the presence of tetrabutylammonium iodide.
3. The protocol of claim 1, wherein said ligating is in the presence of a carbon dioxide bridge or functionally equivalent moiety.
4. The protocol of claim 3, wherein said ligating is in the presence of a carbon dioxide bridge, a carbon disulfide bridge, an alkyl thiocyanate bridge, a carbonyl sulfide bridge, or an isocyanate bridge.
5. The protocol of claim 4, wherein said ligating is in the presence of a carbon dioxide bridge.
6. The protocol of claim 1, wherein the carbonate is an alkyl carbonate.
7. The protocol of claim 1, wherein said alcohol is an aliphatic alcohol.
8. The protocol of claim 1, wherein said electrophile is an alkyl halide.
9. An alkyl carbonate synthesized by the protocol of claim 6.
10. A process for providing carbonates of the general formula

comprising:
   providing an alkyl halide R'—X wherein X is selected from the group consisting of chloride, bromide, iodide, O—Ms and O—Ts, and R' comprises a saturated carbon atom covalently bonded to X;
   providing an alcohol ROH, wherein R is an organic compound; and
   reacting said alkyl halide with said alcohol in an anhydrous solvent containing a base in an amount sufficient to preferentially provide a carbonate, and at a temperature less than 80° C.
11. The process as in claim 10, wherein said base is selected from the group consisting of cesium carbonate, cesium bicarbonate, cesium hydroxide, and mixtures thereof.
12. The process as in claim 10, wherein said base is cesium bicarbonate.
13. The process as in claim 10, wherein said solvent is selected from the group consisting of dimethyl sulfoxide, N,N-dimethyl formamide, NMP and a mixture thereof.
14. The process as in claim 10, further comprising:
   adding tetrabutylammonium iodide.
15. The process as in claim 10, wherein said alkyl halide is covalently attached to an insoluble support matrix during reaction of said alkyl halide with said alcohol.

16. The process as in claim 15, wherein said insoluble support matrix is a Merrifield resin or a Wang resin.

17. A process for providing carbonates of the general formula

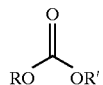

comprising:

providing an alkyl halide R'-X wherein X is selected from the group consisting of chloride, bromide, iodide, O—Ms and O—Ts, and R' comprises a saturated carbon atom covalently bonded to X;

providing an alcohol ROH, wherein R is an organic compound; and reacting said alkyl halide with said alcohol in an anhydrous solvent containing a base in an amount sufficient to preferentially provide a carbonate, and in the presence of carbon dioxide.

18. A protocol for carbonate synthesis comprising:

ligating an organic alcohol to an organic electrophile in the presence of a cesium base and in the presence of carbon dioxide, to form a carbonate.

* * * * *

UNITED STATES PATENT AND TRADEMARK OFFICE
CERTIFICATE OF CORRECTION

PATENT NO. : 6,469,193 B1
DATED : October 22, 2002
INVENTOR(S) : Kyung Woon Jung It is certified that error appears in the above-identified patent and that said Letters Patent is hereby corrected as shown below:

Column 6,
Line 1, "7.19-7.3 (m, 5H);" should read -- 7.19-7.33 (m, 5H); --.

Column 7,
Line 19, "(m, 1H, 7.19-7.32" should read -- (m, 1H), 7.19-7.32 --.
Line 41, "(3.7 mL,0.2 M)" should read -- (3.7 mL, 0.2 M) --.
Line 42, "(230 mg,0.73 mmol," should read -- (230 mg, 0.73 mmol, --.
Line 61, "2.78-2.82 $J_{AB}$=13.5 Hz," should read -- 2.78-2.82 (ABX, $J_{AB}$=13.5 Hz, --.
Line 63, "13C NMR" should read -- $^{13}$C NMR --.
Line 66, "C1$_6$H$_{22}$O$_5$" should read -- $C_{16}H_{22}O_5$ --.

Column 8,
Line 44, "3H, 0.80-0.87(m, 10H),0.94-0.97(m,2H)," should read -- 3H), 0.80-0.87 (m,10H), 0.94-0.97 (m, 2H) --.
Line 45, "1.28-1.35(m,4H)," should read -- 1.28-1.35 (m, 4H), --.

Column 9,
Lines 19-20, "3H), 2H)," should read -- 3H), 1.35-1.46 (m, 2H), --.
Line 42, "N,N-20 dimethylformamide" should read -- N,N-dimethylformamide --.
Line 63, "5.20-7.22-7.45" should read -- 5.20-5.23 (s, 2H); 7.22-7.45 --.
Line 64, "(m,10H)" should read -- (m, 10H) --.

Column 10,
Line 35, "(194mg, 98%)" should read -- (194 mg 98%) --.
Line 42, "19.51,42.36" should read -- 19.51, 42.36 --.

Column 13,
Line 16, "7.32-$^{13}$C NMR" should read -- 7.32-7.35 (m, 5H); $^{13}$C NMR --.
Line 64, "$^{13}$C NMR CDC1$_3$)" should read -- $^{13}$C NMR (90 MHz, CDC1$_3$) --.

Column 14,
Line 21, "6 nmol," should read -- 6 mmol, --.
Line 34, "IR(thinfilm)" should read -- IR (thin film) --.
Line 35, "$^1$HNMR(360" should read -- $^1$H NMR (360 --.
Line 37, "2H, J=4.49" should read -- 2H, J=7.08 Hz), 4.49 --.

UNITED STATES PATENT AND TRADEMARK OFFICE
CERTIFICATE OF CORRECTION

PATENT NO. : 6,469,193 B1
DATED : October 22, 2002
INVENTOR(S) : Kyung Woon Jung It is certified that error appears in the above-identified patent and that said Letters Patent is hereby corrected as shown below:

<u>Column 15,</u>
Lines 64-65, "2H, J=6.08Hz)," should read -- 2H), 5.43 (t, 1H, J=6.08 Hz), --.

<u>Column 16,</u>
Line 5, "C arbonate" should read -- carbonate --.
Lines 46-47, "(A <u>B</u>X," should read -- (A<u>B</u>X, --.

<u>Column 17,</u>
Line 21, "cm$^{-1}$;" should read -- cm$^{-1}$; --.
Line 59, "CH$_2$Cl$_2$(2 mL)" should read -- CH$_2$Cl$_2$ (2 mL) --.
Lines 66-67, "(A <u>B</u>X," should read -- (A<u>B</u>X, --.

<u>Column 18,</u>
Line 1, "5.29(A<u>B</u>X," should read -- 5.29 (A<u>B</u>X, --.
Line 41, "(s,1H)," should read -- (s, 1H), --.

<u>Column 19,</u>
Line 49, "(dd, 1," should read -- (dd, 1H, --.
Line 51, "(m,1H);" should read -- (m, 1H); --.

<u>Column 20,</u>
Line 24, "0.2NHCl" should read -- 0.2 N HCl --.

<u>Column 25,</u>
Line 22, "MeOH/H$_2$O,H$_2$O," should read -- MeOH/H$_2$O, H$_2$O, --.
Lines 63-64, "to the to solution" should read -- to the solution --.

<u>Column 26,</u>
Line 3, "IR3071," should read -- IR 3071, --.
Line 35, "NN-dimethylforamide" should read -- N,N-dimethylforamide --.

UNITED STATES PATENT AND TRADEMARK OFFICE
CERTIFICATE OF CORRECTION

PATENT NO. : 6,469,193 B1
DATED : October 22, 2002
INVENTOR(S) : Kyung Woon Jung It is certified that error appears in the above-identified patent and that said Letters Patent is hereby corrected as shown below:

Column 31,
Line 57, "flitted" should read -- fritted --.

Signed and Sealed this

Fifteenth Day of July, 2003

JAMES E. ROGAN
*Director of the United States Patent and Trademark Office*